(12) United States Patent
Manetsch et al.

(10) Patent No.: US 8,877,752 B2
(45) Date of Patent: Nov. 4, 2014

(54) 4(1H)-QUINOLONES HAVING ANTIMALARIAL ACTIVITY WITH REDUCED CHEMICAL RESISTANCE

(71) Applicants: Roman Manetsch, Tampa, FL (US); Richard Matthew Cross, Brandon, FL (US); Niranjan Kumar Namelikonda, Tampa, FL (US); Dennis Edward Kyle, Lithia, FL (US); Tina Susanna Mutka, Tampa, FL (US); Alexis Nichole LaCrue, Temple Terrace, FL (US); Jordany Richarlson Maignan, Tampa, FL (US); Fabian Ernesto Saenz, Quito (EC)

(72) Inventors: Roman Manetsch, Tampa, FL (US); Richard Matthew Cross, Brandon, FL (US); Niranjan Kumar Namelikonda, Tampa, FL (US); Dennis Edward Kyle, Lithia, FL (US); Tina Susanna Mutka, Tampa, FL (US); Alexis Nichole LaCrue, Temple Terrace, FL (US); Jordany Richarlson Maignan, Tampa, FL (US); Fabian Ernesto Saenz, Quito (EC)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 13/661,300

(22) Filed: Oct. 26, 2012

(65) Prior Publication Data

US 2013/0123258 A1 May 16, 2013

Related U.S. Application Data

(60) Provisional application No. 61/552,609, filed on Oct. 28, 2011.

(51) Int. Cl.
  *C07D 215/233* (2006.01)
  *C07D 413/04* (2006.01)
  *C07D 401/04* (2006.01)
  *C07D 215/56* (2006.01)

(52) U.S. Cl.
  CPC .......... *C07D 215/233* (2013.01); *C07D 413/04* (2013.01); *C07D 401/04* (2013.01); *C07D 215/56* (2013.01)
  USPC ................... 514/235.2; 514/253.07; 514/312; 544/128; 544/363; 546/153; 546/156

(58) Field of Classification Search
None
See application file for complete search history.

(56) References Cited

U.S. PATENT DOCUMENTS 5,081,121 A * 1/1992 Osawa et al. ................. 514/312

OTHER PUBLICATIONS

Price et al., Infrared spectra of 2- and 4-quinolones, 12 Australian J. Chem. 589-600 (1959).*
Winter et al., Antimalarial quinolones: Synthesis, potency, and mechanistic studies, 118(4) Experimental Parasitology 487-497 (2008).*
Cross et al., Endochin Optimization: Structure-Activity and Structure-Property Relationship Studies of 3-Substituted 2-Methyl-4(1H)-quinolones with Antimalarial Activity, 53(19) J. Med. Chem., 7076-7094 (2010) (Publ'd Sep. 9, 2010).*

* cited by examiner

*Primary Examiner* — Janet L Andres
*Assistant Examiner* — Timothy R Rozof
(74) *Attorney, Agent, or Firm* — Thomas | Horstemeyer, L.L.P.

(57) ABSTRACT

Provided are 4(1H)-quinolone derivatives effective in inhibiting or eliminating the viability of at least one of the stages in the life-cycle of the malarial parasite, and to show a reduced propensity to induce resistance to the compound by the target parasite. In particular, the compounds can be derivatives of phenoxyethoxy-quinolones, and including, but not only, 7-(2-phenoxyethoxy)quinolin derivatives. These compounds may be administered by themselves, with at least one other derivative compound, or with other antimalarial compounds, to an animal or human subject. The therapeutic compositions can be and formulated to reduce the extent of a *Plasmodium* infection in the recipient subject, or to reduce the likelihood of the onset or establishment of a *Plasmodium* infection if administered prior to the parasite contacting the subject. The therapeutic compositions can be formulated to provide an effective single dose amount of an antimalarial compound or multiple doses for administering over a period of time.

11 Claims, 10 Drawing Sheets

| Compound | R¹ | R² | R³ | R⁴ | EC₅₀ W2 (nM) | EC₅₀ TM90-C2B (nM) | RI | EC₅₀ J774 (μM) |
|---|---|---|---|---|---|---|---|---|
| 5 | -CO₂Me | PhO(CH₂)₃- | -Bu | -H | 0.05 | 11.2 | 223 | 46 |
| 14 | -CO₂Me | -MeO | -Cl | -H | 134 | 765 | 5.7 | 37 |
| 15 | -H | PhO(CH₂)₃- | -Bu | -Me | 216 | 44.1 | 0.20 | 28 |
| 16 | -Et | PhO(CH₂)₃- | -Bu | -Me | 1.92 | 0.15 | 0.08 | 1 |
| 27 | -Et | PhO(CH₂)₃- | -H | -Me | 104 | 71.3 | 0.79 | 4 |
| 17 | -Et | PhO(CH₂)₃- | -Cl | -Me | 256 | 72.1 | 0.28 | >28 |
| 25 | -Et | PhO(CH₂)₃- | -Br | -Me | 203 | 43.5 | 0.21 | >25 |
| 18 | -Et | PhO(CH₂)₃- | -Me | -Me | 255 | 27.7 | 0.11 | >30 |
| 19 | -Et | PhO(CH₂)₃- | -MeO | -Me | 184 | 19.5 | 0.11 | >29 |
| 20 | -Et | MeO(CH₂)₃- | -Cl | -Me | 908 | 79.7 | 0.09 | 19 |
| 21 | -Et | nBu(CH₂)₃- | -Cl | -Me | 8450 | 776 | 0.09 | N.D. |
| 22 | -Et | (branched) | -Cl | -Me | 6130 | 6130 | 1.0 | N.D. |
| 23 | -Et | morpholino(CH₂)₃- | -Cl | -Me | 5090 | 726 | 0.14 | N.D. |
| 24 | -Et | Me₂N(CH₂)₃- | -Cl | -Me | 5050 | 604 | 0.12 | N.D. |
| 26 | -Et | furyl-CH₂O(CH₂)₂- | -Cl | -Me | 976 | 91.7 | 0.09 | >23 |

| Compound | Ar | EC$_{50}$ W2 (nM) | EC$_{50}$ TM90-C2B (nM) | RI | EC$_{50}$ J774 (μM) |
|---|---|---|---|---|---|
| 31 | | 1070 | 764 | 0.71 | 23 |
| 32 | | 3150 | 1016 | 0.33 | 23 |
| 33 | | 1350 | 588 | 0.44 | 23 |
| 34 | | 509 | 2450 | 4.82 | 20 |
| 35 | | 3220 | 2510 | 0.78 | 20 |
| 36 | | 1390 | 1002 | 0.72 | 19 |
| 37 | | 4050 | 4050 | 1.00 | 16 |
| 38 | | 58.5 | 475 | 8.12 | 16 |
| 39 | | 71.8 | 140 | 1.95 | 20 |
| 40 | | 907 | 1630 | 1.79 | 22 |
| 41 | | 27.9 | 30.9 | 1.11 | 19 |
| 42 | | 68.7 | 542 | 7.89 | >21 |
| 43 | | 27.0 | 128 | 4.73 | 22 |

*Fig. 6*

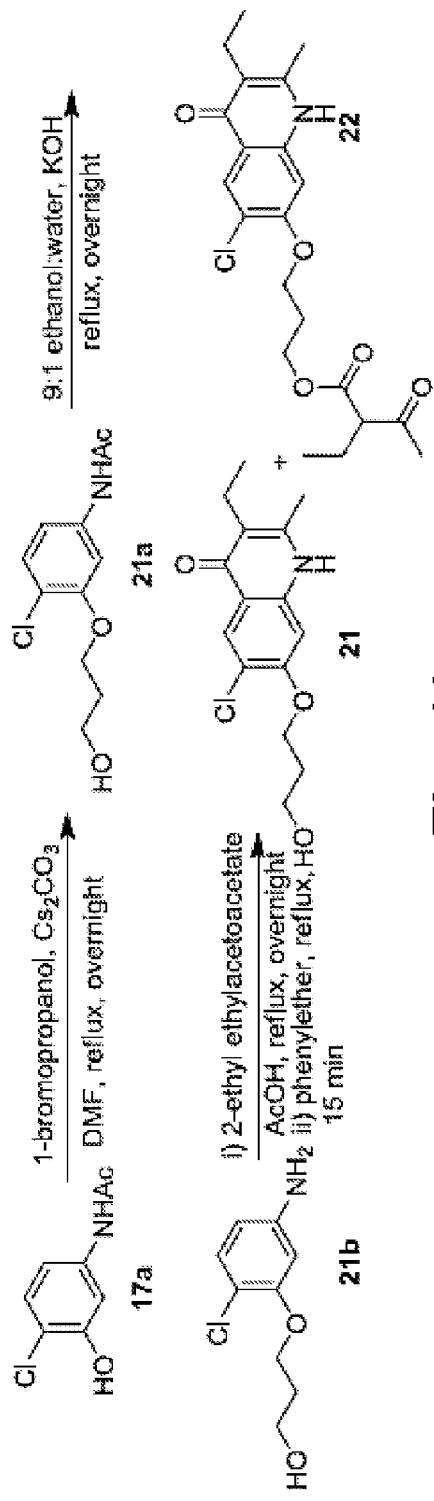
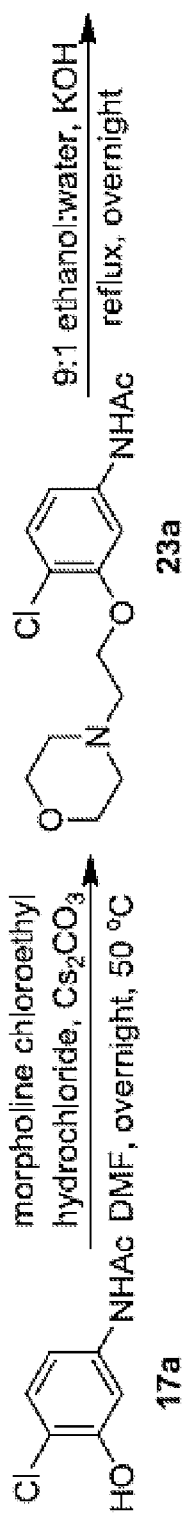
Fig. 11
Fig. 12

4(1H)-QUINOLONES HAVING ANTIMALARIAL ACTIVITY WITH REDUCED CHEMICAL RESISTANCE

CROSS-REFERENCE TO RELATED APPLICATIONS

This application claims priority to U.S. Provisional Patent Application Ser. No. 61/552,609 entitled "4(1H)-QUINOLONES HAVING ANTIMALARIAL ACTIVITY WITH REDUCED CHEMICAL RESISTANCE" and filed Oct. 28, 2011, the entirety of which is hereby incorporated by reference.

STATEMENT ON FUNDING PROVIDED BY THE U.S. GOVERNMENT

This invention was made with government support under NIH Grant No. R01GM097118 awarded by the U.S. National Institutes of Health, National Institute of General Medical Sciences. The government has certain rights in the invention.

TECHNICAL FIELD

The present disclosure is generally related to compounds and compositions comprising thereof effective in reducing the viability of at least one stage of the malarial parasite. The present disclosure is further related to methods of reducing or preventing the onset of a malarial infection in an animal or human.

BACKGROUND

Malaria is among the most significant public health problems in the world. The disease occurs in tropical and subtropical climates and affects over two million people annually while claiming nearly one million lives in 2009 (Wells et al., (2009) *Nat. Rev. Drug Discovery* 8: 879-891). *P. falciparum* and *P. vivax* are the two most prevalent species responsible for causing disease in humans. The development of curative antimalarial agents is difficult because of the various developmental stages of the parasite within the host. Following inoculation of sporozoites by an infected female *Anopheles* mosquito, the parasite must first undergo a proliferation period within the liver before the pathogenic infection of red blood cells ensues.

The most effective drug for liver stage infections is primaquine, an 8-aminoquinoline that acts on actively-growing liver stages and on the dormant forms known as hypnozoites that can lay dormant in a host for weeks to years and upon reactivation cause a relapse. Discovery and development of drugs active against hypnozoites are limited by the lack of reliable high or medium throughput assays. New drugs are, therefore, required that are safe and effective against liver and blood stage parasites simultaneously within the same host.

An additional difficulty for malaria drug development is the rapid emergence of multidrug resistance. Many of the common antimalarials such as atovaquone, chloroquine, and more recent artemisinin combination therapies (ACTs) have suffered from parasitological resistance being developed in many regions of the world, especially in Southeast Asia.

Advances in drug discovery such as high-throughput screening, physicochemical property assessment, synthetic methodologies, and improved in vivo efficacy protocols have allowed for re-examining old chemotypes or hits and for optimizing them to a more appropriate lead clinical candidate. Thus, endochin (1), a 4(1H)-quinolone, and its related tetrahydroacridone analogue (THA) floxacrine (2) were successfully optimized for antimalarial activity by substituting various benzenoid ring features and aryl moieties ((3) and (4)) while simultaneously assessing the physicochemical properties (FIG. 1).

Another such example is the 4(1H)-quinolone ester ICl 56,780 (5), which was found to have antimalarial activity (Ryley & Peters (1970) *Ann. Trop. Med. Parasitol.* 64: 209-222). This compound possesses blood schizontocidal activity against *P. berghei* and prophylactic activity against *P. cynomolgi* sporozoite challenge assays. It was shown that rhesus monkeys inoculated intravenously with *P. cynomolgi* sporozoites and subsequently treated for 5 to 7 consecutive days had no relapse after 120 days of exposure, confirming potency against hypnozoites. Compound (5) was found to be curative at 15 mg/kg. Unfortunately, rapid selection of resistance was obtained after one passage in *P. berghei* infected mice, leading to an abandonment of the compound.

The in vivo anti-relapse activity in combination with the excellent blood stage activity of (5) shows great promise in developing a viable multistage antimalarial agent. A related set of 4-oxo-3-carboxyl analogues (6) were recently developed by using a parallel approach of SAR and pharmacologic characterization to design quinolones that were less prone to cross-resistance with atovaquone.

SUMMARY

The disclosure provides variant 4(1H)-quinolones and 7-(2-phenoxyethoxy)-4(1H)-quinolones (PEQs) scaffolds to optimize SPR and blood stage antimalarial activity. Since the rapid induction of resistance reported in *P. berghei* was likely due to cytochrome b mutations, the scaffolds were also optimized for potency against clinically relevant atovaquone resistant *P. falciparum*. Accordingly, one aspect of the disclosure encompasses embodiments of a compound having the Formula I or II:

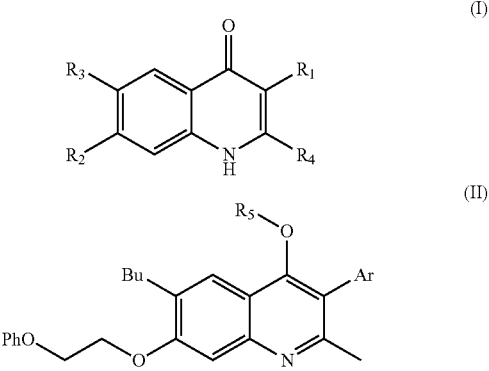

Another aspect of the disclosure encompasses therapeutic compositions comprising at least one of the 4(1H)-quinolone compounds of the disclosure and in an amount that is effective, when administered to an animal or human subject as a single dose or as a series of doses, in reducing or eliminating a malarial parasite infection in the subject animal or human, or prophylactically prevents the establishment of such an infection.

Another aspect of the disclosure encompasses embodiments of a method of reducing the viability of a population of malarial parasites, wherein the method comprises administering to an animal or human subject a therapeutically effective amount of a pharmaceutically acceptable composition comprising at least one of the 4(1H)-quinolone compounds of the disclosure.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 6 shows a table listing the $EC_{50}$ values of 3-Aryl PEQs. Dihydroartemisinin (DHA), chloroquine (CQ), and atovaquone (ATO) were internal controls for each in vitro assay. DHA (1.8 nM W2 and 0.9 nM TM90-C2B), CQ (131 nM W2 and 162 nM TM90-C2B), and ATO (0.53 nM W2 and >170 nM TM90-C2B).

FIG. 11 schematically illustrates the synthesis of compound 21 and 22.

FIG. 12 schematically illustrates the synthesis of compound 23.

Figure 1:
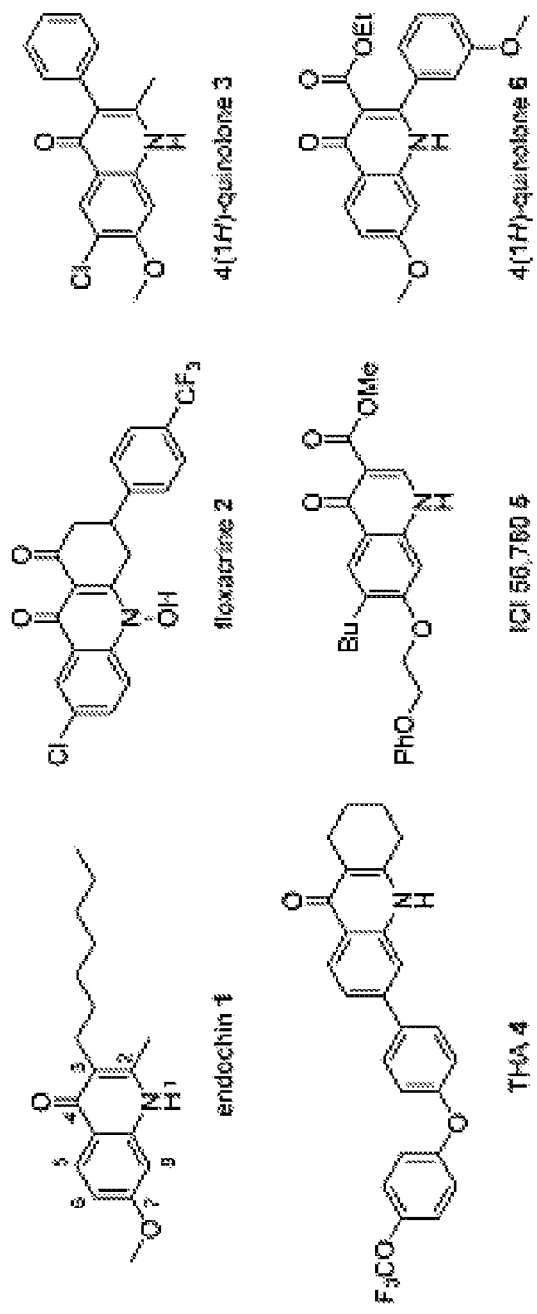
FIG. 1 shows the structures of prior art antimalarial compounds (1)-(6).

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Abbreviations

PEQ, phenoxyethoxy-quinolone; $AlCl_3$, aluminum chloride; $NaBH_4$, sodium borotetrahydride; THF, tetrahydrofuran; AcOH, acetic acid; TFA, trifluoracetic acid; NaH, sodium hydride; DMSO, dimethyl sulfoxide; DMF, dimethylformamide; $BBR_3$, born tribromide; $Pd_2(dba)_3$, Tris(dibenzylideneacetone)dipalladium(0); SPhos, 2-Dicyclohexylphosphino-2',6'-dimethoxybiphenyl; DHA, dihydroartemisinin; CQ, chloroquine; ATO, atovaquone; EtI, ethyl iodide; MeI, methyl iodide; $ArB(OH)_2$, aryl boronic acid; RI, resistance index.

Definitions

The terms "administration of" and "administering" a compound or composition as used herein refers to providing a compound of the disclosure or a prodrug of a compound of the disclosure to the individual in need of treatment. The compounds of the present disclosure may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The term "delivering to a cell" as used herein refers to the direct targeting of a cell with a small molecule compound, a nucleic acid, a peptide or polypeptide, or a nucleic acid capable of expressing an inhibitory nucleic acid or polypeptide by systemic targeted delivery for in vivo administration, or by incubation of the cell or cells with said effector ex vivo or in vitro.

The terms "treat" or "treatment" as used herein refer to both therapeutic treatment and prophylactic or preventative measures, where the object is to prevent or slow down (lessen) an undesired physiological change or disorder resulting from a seizure including, but not limited to, cellular apoptosis or cell death, and especially, but not limited to, a reduction in the viability of a neural cell. Beneficial or desired clinical results include, but are not limited to, alleviation of symptoms, diminishment of the extent of disease, stabilized (i.e., not worsening) state of disease, and delay or slowing of progression of the symptoms recognized as originating from a stroke. The term "treatment" can also refer to prolonging survival as compared to expected survival if not receiving treatment. Those in need of treatment include those already with the condition or disorder as well as those prone to have the condition or disorder or those in which the condition or disorder is to be prevented or onset delayed.

The term "composition" as used herein refers to a product comprising the specified ingredients in the specified amounts, as well as any product which results, directly or indirectly, from combination of the specified ingredients in the specified amounts. Such a term in relation to a pharmaceutical composition is intended to encompass a product comprising the active ingredient(s), and the inert ingredient(s) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure and a pharmaceutically acceptable carrier.

When a compound of the present disclosure is used contemporaneously with one or more other drugs, a pharmaceutical composition containing such other drugs in addition to the compound of the present disclosure is contemplated. Accordingly, the pharmaceutical compositions of the present disclosure include those that also contain one or more other active ingredients, in addition to a compound of the present disclosure. The weight ratio of the compound of the present disclosure to the second active ingredient may be varied and will depend upon the effective dose of each ingredient. Generally, an effective dose of each will be used. Thus, for example, but not intended to be limiting, when a compound of the present disclosure is combined with another agent, the weight ratio of the compound of the present disclosure to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used. In such combinations the compound of the present disclosure and other active agents may be administered separately or in conjunction. In addition, the administration of one element may be prior to, concurrent to, or subsequent to the administration of other agent(s).

The terms "effective amount," "therapeutically-effective amount," and "therapeutically effective dose" as used herein refer to the amount of a compound, material, or composition comprising a compound or composition of the present disclosure, and which is effective for producing a desired therapeutic effect, biological or medicinal response in a tissue system, animal or human that is being sought by a researcher, veterinarian, medical doctor or other clinician, which includes alleviation of the symptoms of the disease or disorder being treated or a reduction in a side-effect due to an administered pharmaceutical agent.

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically-acceptable carrier" as used herein refers to a pharmaceutically-acceptable material, composition or vehicle, such as a liquid or solid filler, diluent, excipient, solvent or an encapsulating material such as liposomes, polyethylene glycol (PEG), PEGylated liposomes, nanoparticles and the like, involved in carrying or transporting the subject compositions or therapeutic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "excipient" as used herein refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The term "subject" as used herein refers to mammals, and especially humans, in need of treatment.

The term "unit dosage form" as used herein refers to physically discrete units suitable as unitary dosages for human patients and other mammals with each unit containing a predetermined quantity of active material calculated to produce the desired therapeutic effect in association with suitable pharmaceutical carriers or excipients. The compositions according to the present disclosure may be formulated in a unit dosage form. A single daily unit dose also may be divided into 2 or 3 unit doses that are taken at different times throughout the day, or as a controlled release form, so as to reduce adverse side-effects as much as possible.

The term "alkyl" as used herein refers to $C_{1-20}$ inclusive, linear (i.e., "straight-chain"), branched, or cyclic, saturated or at least partially and, in some cases, fully unsaturated (i.e., alkenyl and alkynyl)hydrocarbon chains including, for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain.

"Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

The term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" as used herein refers to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

The term "substituted aryl" includes aryl groups, as defined herein, in which one or more atoms or functional groups of the aryl group are replaced with another atom or functional group including, for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "acyl" as used herein refers to an organic acid group wherein the —OH of the carboxyl group has been replaced with another substituent (i.e., as represented by RCO—, wherein R is an alkyl or an aryl group as defined herein). The term "acyl" specifically includes arylacyl groups, such as an acetylfuran and a phenacyl group. Specific examples of acyl groups include acetyl and benzoyl.

The terms "cyclic" and "cycloalkyl" as used herein refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur, or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The terms "alkoxyl" or "alkoxyalkyl" as used herein refer to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

The term "aryloxyl" as used herein refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

The term "aralkyl" as used herein refers to an aryl-alkyl- group wherein aryl and alkyl are as previously described, and included substituted aryl and substituted alkyl. Exemplary aralkyl groups include benzyl, phenylethyl, and naphthylmethyl.

The term "aralkyloxyl" as used herein refers to an aralkyl-O— group wherein the aralkyl group is as previously described. An exemplary aralkyloxyl group is benzyloxyl.

The term "dialkylamino" as used herein refers to an —NRR' group wherein each of R and R' is independently an alkyl group and/or a substituted alkyl group as previously described. Exemplary alkylamino groups include ethylmethylamino, dimethylamino, and diethylamino.

The term "alkoxycarbonyl" as used herein refers to an alkyl-O—CO— group. Exemplary alkoxycarbonyl groups include methoxycarbonyl, ethoxycarbonyl, butyloxycarbonyl, and t-butyloxycarbonyl.

The term "aryloxycarbonyl" as used herein refers to an aryl-O—CO— group. Exemplary aryloxycarbonyl groups include phenoxy- and naphthoxy-carbonyl.

The term "aralkoxycarbonyl" as used herein refers to an aralkyl-O—CO— group. An exemplary aralkoxycarbonyl group is benzyloxycarbonyl.

The term "carbamoyl" as used herein refers to an $H_2N$—CO— group.

The term "alkylcarbamoyl" as used herein refers to a R'RN—CO— group wherein one of R and R' is hydrogen and the other of R and R' is alkyl and/or substituted alkyl as previously described.

The term "dialkylcarbamoyl" as used herein refers to a R'RN—CO— group wherein each of R and R' is independently alkyl and/or substituted alkyl as previously described.

The term "acyloxyl" as used herein refers to an acyl-O— group wherein acyl is as previously described.

The term "acylamino" as used herein refers to an acyl-NH— group wherein acyl is as previously described.

The term "aroylamino" as used herein refers to an aroyl-NH— group wherein aroyl is as previously described.

The term "amino" as used herein refers to the —NH$_2$ group.

The term "carbonyl" as used herein refers to the —(C=O)— group.

The term "carboxyl" refers to the —COOH group.

The terms "halo," "halide," or "halogen" as used herein refer to fluoro, chloro, bromo, and iodo groups.

The term "hydroxyl" as used herein refers to the —OH group.

The term "hydroxyalkyl" as used herein refers to an alkyl group substituted with an —OH group.

The term "mercapto" as used herein refers to the —SH group.

The term "oxo" as used herein refers to a compound described previously herein wherein a carbon atom is replaced by an oxygen atom.

The term "nitro" as used herein refers to the —NO$_2$ group.

The term "thio" as used herein refers to a compound described previously herein wherein a carbon or oxygen atom is replaced by a sulfur atom.

The term "sulfate" as used herein refers to the —SO$_4$ group.

The term "reflux" and grammatical derivations thereof as used herein refer to boiling a liquid, such as a solvent, in a container, such as a reaction flask, with which a condenser is associated, thereby facilitating continuous boiling without loss of liquid, due to the condensation of vapors on the interior walls of the condenser.

The term "aprotic solvent" as used herein refers to a solvent molecule, which can neither accept nor donate a proton. Typical aprotic solvents include, but are not limited to, acetone, acetonitrile, benzene, butanone, butyronitrile, carbon tetrachloride, chlorobenzene, chloroform, 1,2-dichloroethane, dichloromethane, diethyl ether, dimethylacetamide, N,N-dimethylformamide (DMF), dimethylsulfoxide (DMSO), 1,4-dioxane, ethyl acetate, ethylene glycol dimethyl ether, hexane, N-methylpyrrolidone, pyridine, tetrahydrofuran (THF), and toluene. Certain aprotic solvents are polar solvents. Examples of polar aprotic solvents include, but are not limited to, acetone, acetonitrile, butanone, N,N-dimethylformamide, and dimethylsulfoxide. Certain aprotic solvents are non-polar solvents. Examples of nonpolar, aprotic solvents include, but are not limited to, diethyl ether, aliphatic hydrocarbons, such as hexane, aromatic hydrocarbons, such as benzene and toluene, and symmetrical halogenated hydrocarbons, such as carbon tetrachloride.

The term "protic solvent" as used herein refers to a solvent molecule, which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water.

The term "acid anhydride" as used herein refers to an anhydride of an organic acid and includes, but is not limited to acetic anhydride (($CH_3C$=O)$_2$O or $Ac_2O$) and benzoic anhydride (($C_6H_5C$=O)$_2$O).

The terms "*Plasmodium* parasite" and "*Plasmodium* organism" as used herein refer to any member of the protozoan genus *Plasmodium* including, but not limited to, the four species that cause human malaria: *P. vivax, P. malariae, P. falciparum*, and *P. ovale*. The corresponding "vertebrate host" is a human or other secondary host that is susceptible to infection by the wild-type *Plasmodium* parasite. Malaria infection is initiated by *Plasmodium* sporozoites in the salivary glands of mosquitoes. These sporozoites invade hepatocytes of the vertebrate host and differentiate into liver stage (LS) forms. After a few days the LS parasites produce several thousand merozoites that are released from the hepatocytes and invade erythrocytes to start the blood stage cycle that causes malaria disease.

Description

The present disclosure encompasses quinolone derivatives that are effective in inhibiting or eliminating the viability of at least one of the stages in the life-cycle of the malarial parasite, and that advantageously show a reduced ability to generate resistance to the compound by the target parasite. In particular, the present disclosure encompasses embodiments of phenoxyethoxy-quinolones, and especially 7-(2-phenoxyethoxy)quinolin derivatives. It is contemplated that the compounds of the disclosure may be administered by themselves, with at least one other analogous compound according to the disclosure, or with other antimalarial compounds, to an animal or human subject to reduce the extent of a *Plasmodium* infection in the recipient subject, or to reduce the likelihood of the onset or establishment of a *Plasmodium* infection if administered prior to the parasite contacting the subject. Accordingly, the compounds of the disclosure may be formulated into pharmaceutically acceptable compositions to provide an effective dose amount of said compound when administered to a subject animal or human in need either as a single dose or as multiple doses administered over a period of time.

Compound 5 was first synthesized to obtain preliminary data on the PEQ scaffold by obtaining more than 100 g of the intermediate aniline 12 to funnel into Conrad-Limpach reaction sequences to generate analogues of 5. Iodination of a PEQ scaffold to prepare 3-aryl analogues could be achieved according to Cross & Manetsch (2010) *J. Org. Chem.* 75: 8654-8657, incorporated herein by reference in its entirety. Furthermore, aniline precursors were used in several iterative sequences to prepare structurally diverse analogues in the 6- and 7-positions.

Figure 2:
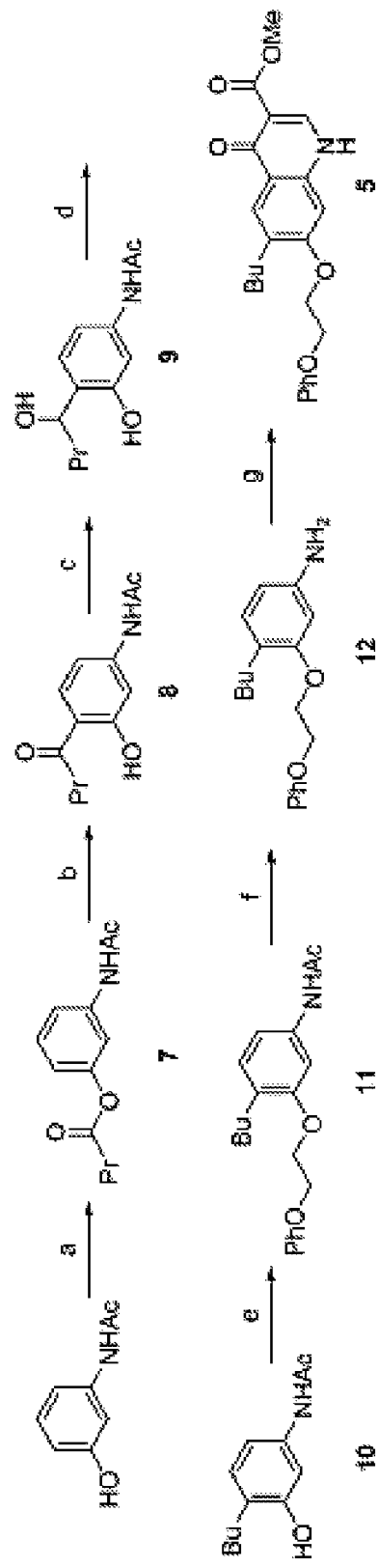
FIG. 2 schematically shows the synthesis of the PEQ 5 via key intermediate aniline 11a. Reaction conditions: (a) butyryl chloride, pyridine, room temperature; (b) $AlCl_3$, 150-175° C., 45 min, then 3 hrs; (c) $NaBH_4$, THF anhydrous, 0° C.; (d) AcOH, 10% Pd/C, 60 psi, 36 hrs; (e) NaH, DMF, 30 mins, then (2-bromoethoxy)benzene, 3 hrs; (f) KOH (14 equiv), EtOH/$H_2O$ (9:1), reflux, 4 hrs; (g) dimethyl 2-(methoxymethylene)malonate, EtOH, reflux; (h) $Ph_2O$, reflux, 12 mins.

The route to generate 5 began with 450 g of commercially available N-(3-hydroxyphenyl)acetamide that was transformed to 7 with butyryl chloride in pyridine, as shown in FIG. 2. Next a Fries rearrangement was employed to arrive at 8 using $AlCl_3$. Compound 8 was reduced using $NaBH_4$ to obtain benzylic alcohol 9 in moderate yield and high purity. Compound 9 was now more prone to hydrogenolysis compared to the conjugated ketone 8, and the hydrogenation in acetic acid at 60 psi yielded 10. Compound II was prepared through a simple alkylation using (2-bromoethoxy)benzene in high yield. The aniline intermediate 12 was prepared via hydrolysis of the acetamido moiety in 11. Finally, 5 was synthesized in a two-step Gould-Jacobs sequence from 12. The compound was isolated via precipitation and recrystallized in DMF/methanol (4:1).

Figure 3:
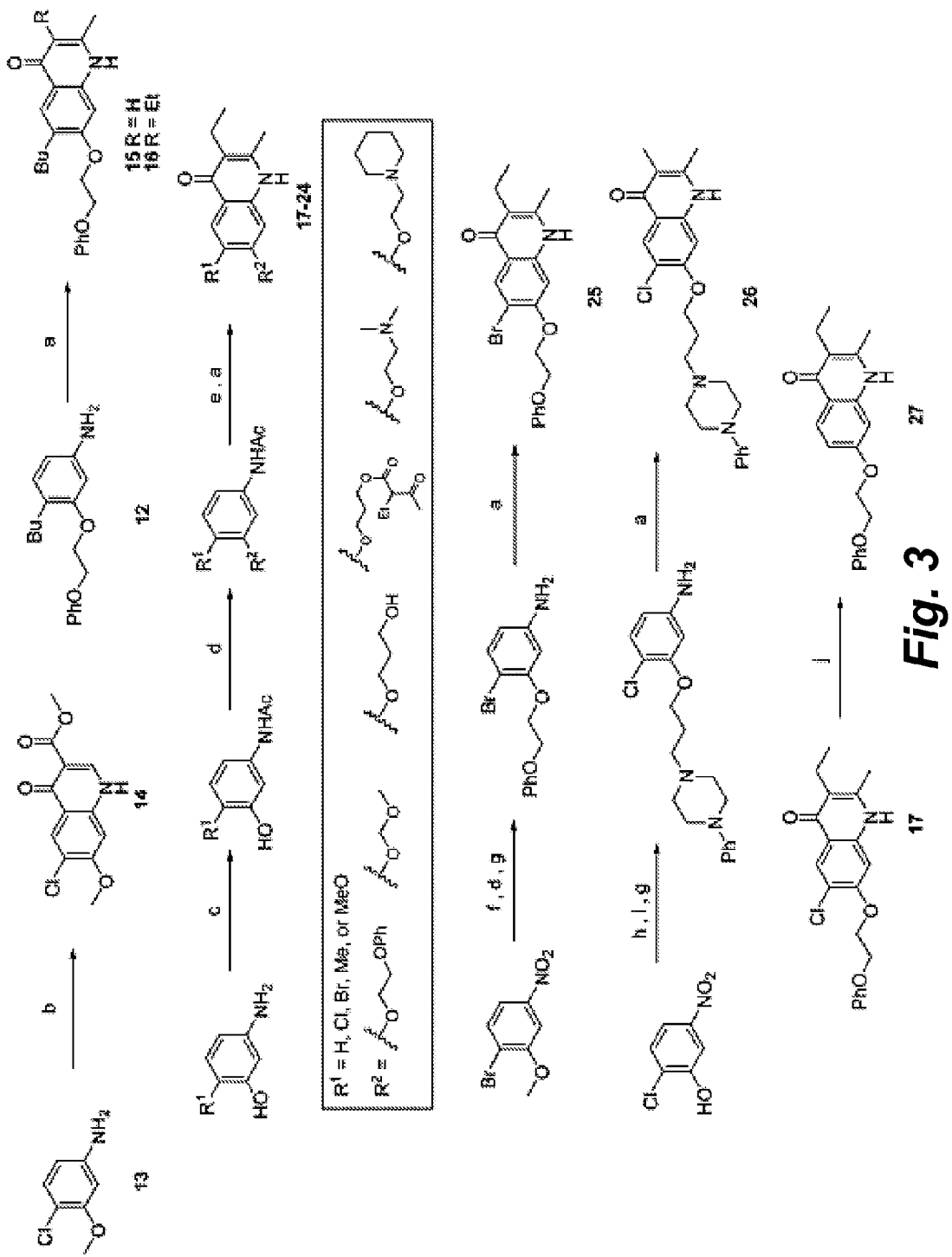
FIG. 3 schematically shows the synthesis of 4(1H)-quinolones 13-27a. Reaction conditions: (a) Ethyl acetoacetate or 2-ethyl acetoacetate, AcOH, benzene, Dean-Stark trap, reflux, overnight, then $Ph_2O$, reflux, 15 mins; (b) 1-ethyl 3-methyl-2-acetylmalonate, AcOH, benzene, Dean-Stark trap, reflux, overnight, then $Ph_2O$, reflux, 15 mins; (c) $Ac_2O$, AcOH; (d) corresponding alkyl halide, $Cs_2CO_3$, DMF, 4-8 hrs; (e) KOH, EtOH/$H_2O$ (9:1), reflux; (f) $BBr_3$; (g) Zn, AcOH, room temperature, 4 hrs; (h) 1,3-dibromopropane, $Cs_2CO_3$, room temperature; (i) N-phenylpiperazine, $K_2CO_3$, DMF, room temperature; (j) $Pd_2(dba)_3$, SPhos, $K_3PO_4$, DMF, mesitylboronic acid, 130° C.
Figure 4:
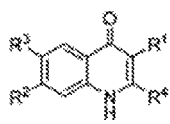
FIG. 4 shows a table listing the $EC_{50}$ values of PEQ analogues. Dihydroartemisinin (DHA), chloroquine (CQ), and atovaquone (ATO) were internal controls for each in vitro assay. DHA (1.8 nM W2 and 0.9 nM TM90-C2B), CQ (131 nM for TM90-C2B and 162 nM for W2), and ATO (0.53 nM W2 and greater than 170 nM TM90-C2B). N.D.: not determined.

Starting from the aniline 13, a 6-chloro-7-methoxy-4(1H)-quinolone bearing the β-dicarbonyl moiety (14) was synthesized using 1-ethyl 3-methyl 2-acetyl-malonate. A subset of 5 was prepared to determine the necessity of the methyl 3-benzoate substituent, as shown in FIGS. 3 and 4. The placement of a proton or ethyl group in the 3-position compared to a methyl 3-benzoate substituent would determine the importance of the β-dicarbonyl motif present in 5. Compound 12 was subjected to Conrad-Limpach conditions using two different 2-substituted β-ketoesters to generate 15 and 16.

A set of 3-ethyl-4(1H)-quinolones substituted at the 6- or 7-position was also prepared. The 6- or 7-substitution contained various solubilizing groups with different linker lengths. Starting from 5-amino-2-chlorophenol, 4(1H)-quinolones 17-24 were prepared, as illustrated in FIG. 3 and listed in FIG. 4. N-Acylation of 5-amino-2-substituted phenols produced an intermediate acetamide, which could be alkylated using various alkyl halides. These intermediates were then hydrolyzed using KOH to arrive at the necessary anilines. The anilines were then cyclized using 2-ethyl-β-ketoester to yield the corresponding 4(1H)-quinolones 17-24.

An alternative route was used to prepare 25-27 utilizing a commercially available disubstituted nitro precursor. Compound 26 was initially synthesized via an acetamide intermediate as in FIG. 3. 1,3-dibromopropane (condition h, FIG. 3) led to inseparable mixtures of the aniline required to prepare 26 and an O-allyl side product generated from elimination using cesium carbonate. Employment of 2-chloro-5-nitrophenol as the starting material led to overall improved yields and easier separation of elimination side products. The synthesis of 27 started from 17 using several standard Pd hydrogenation conditions and resulted in a mixture consisting of 27 and a 4(1H)-quinolone product containing a partially reduced benzenoid ring. Cross-couplings of 3-halo-4(1H)-quinolone with mesitylboronic acid yielded mainly the protodehalogenated 4(1H)-quinolone (Cross & Manetsch (2010) *J. Org. Chem.* 75: 8654-8657). Accordingly, 17 was heated in a Schlenk tube for 36 hrs with several additions of mesitylboronic acid until the chlorine was all consumed, thereby generating 27 with improved yields.

Figure 5:
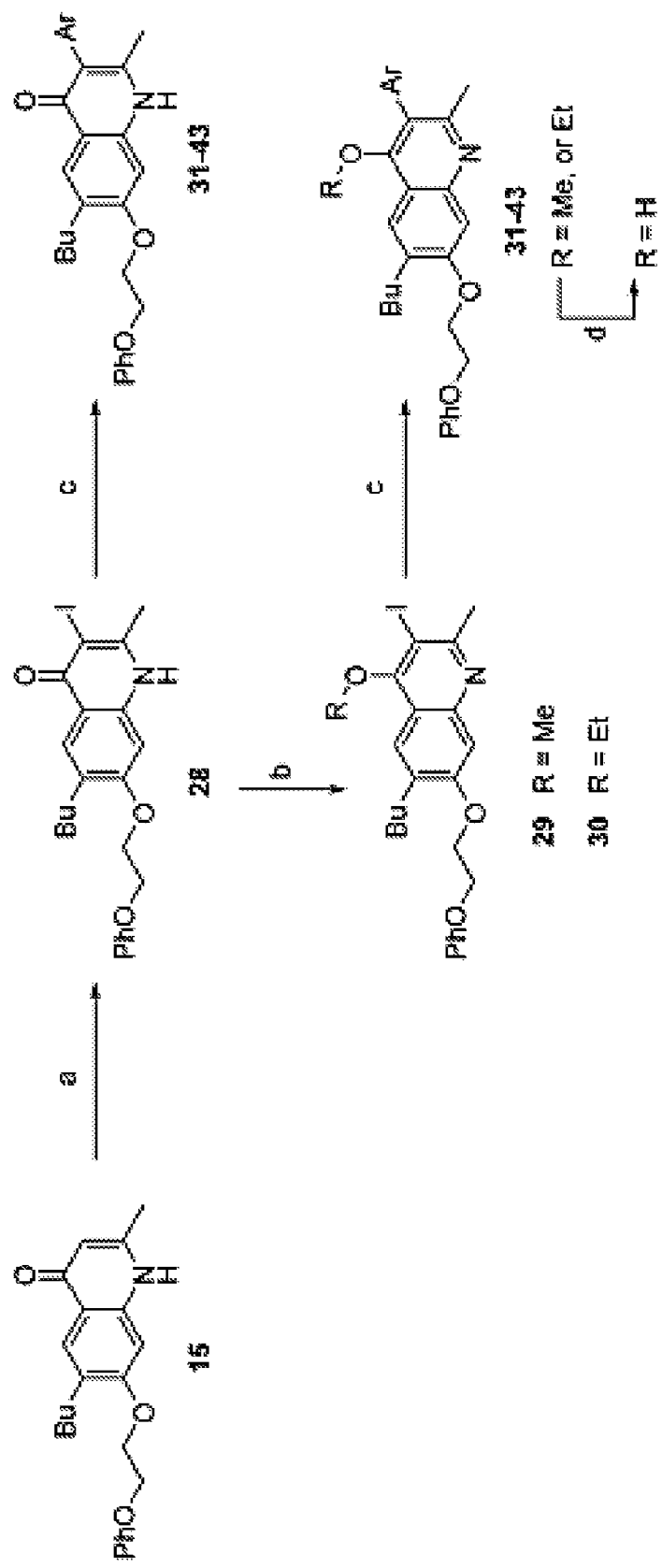
FIG. 5 schematically shows the synthesis of 3-Aryl PEQs. Reaction conditions: (a) KI (20% aqueous), $I_2$, 2 M NaOH, MeOH, room temperature, 2 hrs; (b) $Cs_2CO_3$, DMF, EtI/MeI, 0° C. to room temperature, 5 hrs; (c) $Pd_2(dba)_3$, SPhos, $K_3PO_4$, DMF, ArB(OH)$_2$, 110° C. or Pd(PPh$_3$)$_4$, 2M $Na_2CO_3$, DMF, ArB(OH)$_2$, 110° C. (MW); (e) HBr/AcOH, reflux 1-2 hrs.
Figure 7:
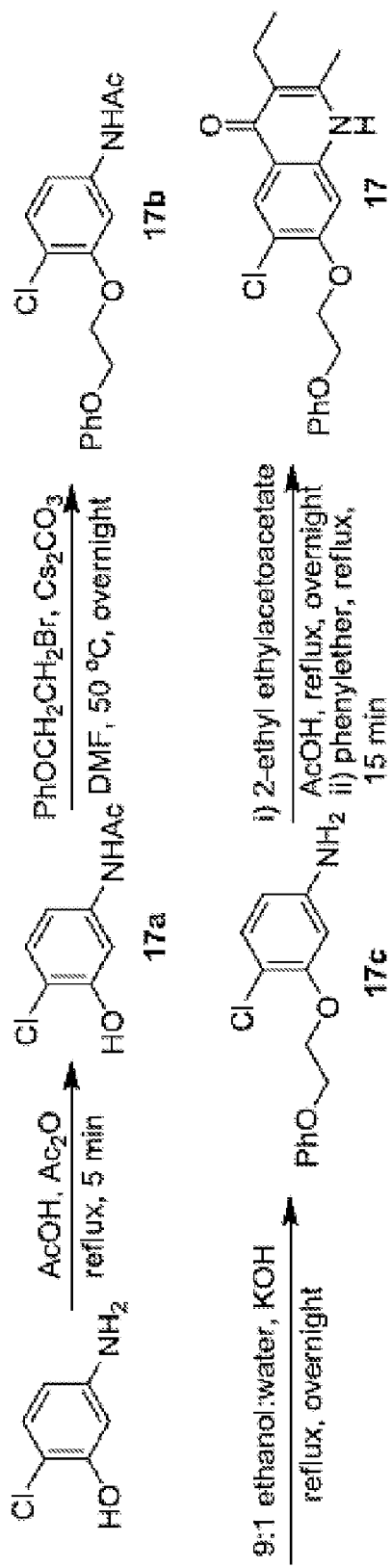
FIG. 7 schematically illustrates the synthesis of compound 17.
Figure 8:
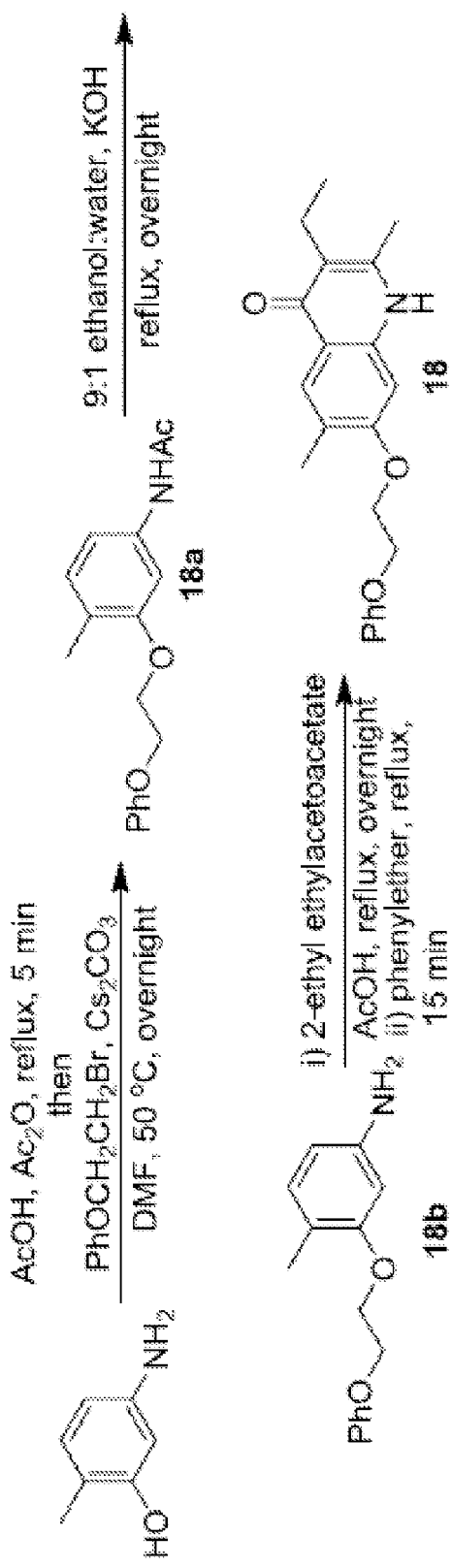
FIG. 8 schematically illustrates the synthesis of compound 18.
Figure 9:
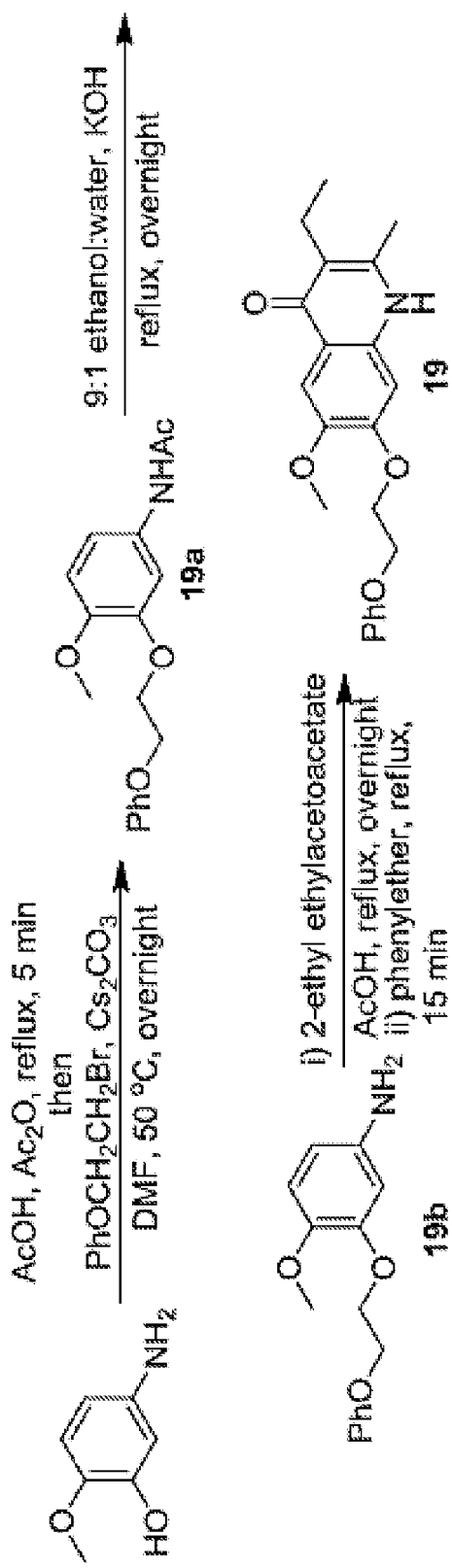
FIG. 9 schematically illustrates the synthesis of compound 19.
Figure 10:
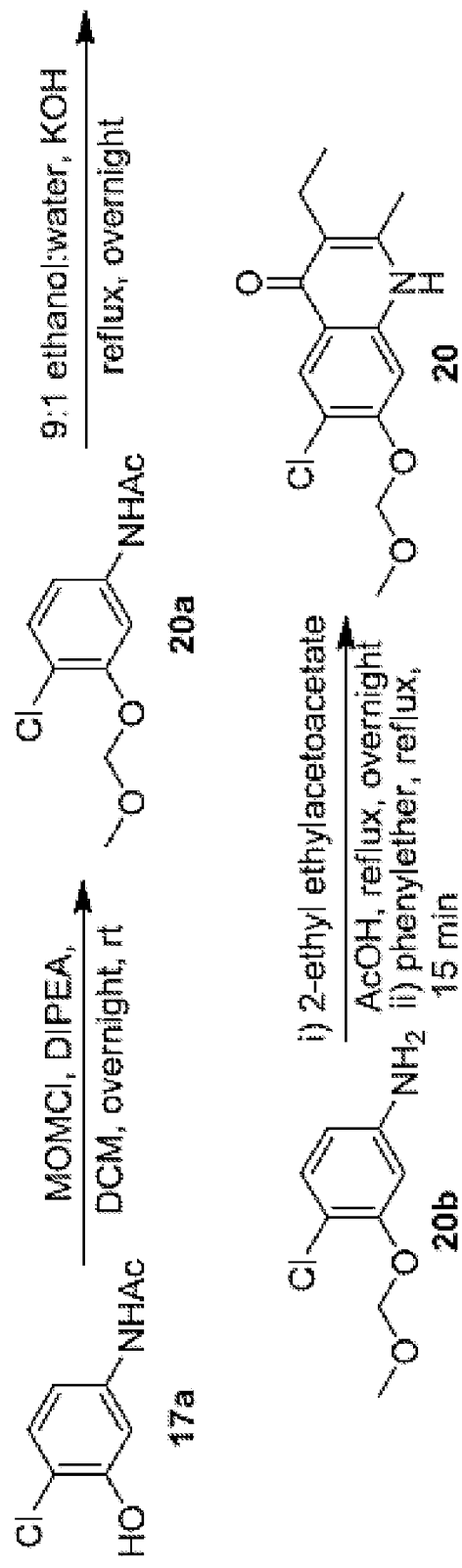
FIG. 10 schematically illustrates the synthesis of compound 20.
Figure 13:
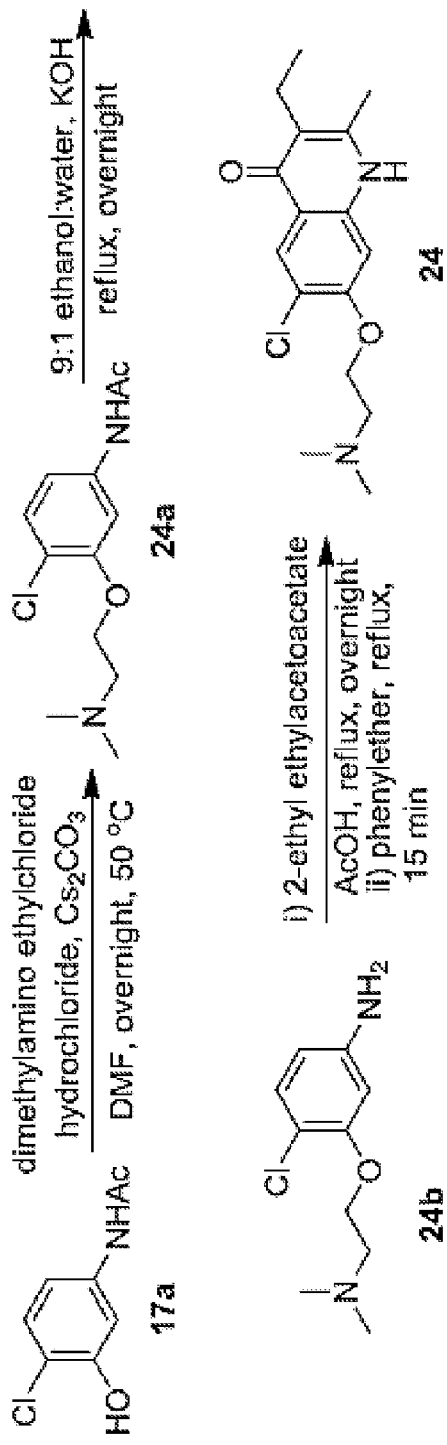
FIG. 13 schematically illustrates the synthesis of compound 24.
Figure 14:
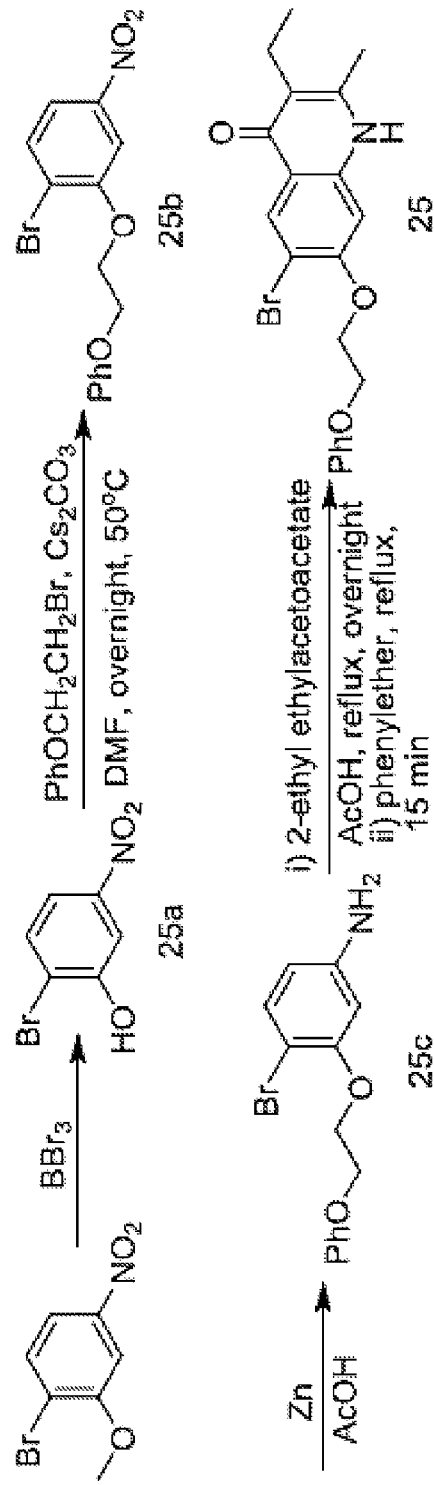
FIG. 14 schematically illustrates the synthesis of compound 25.
Figure 15:
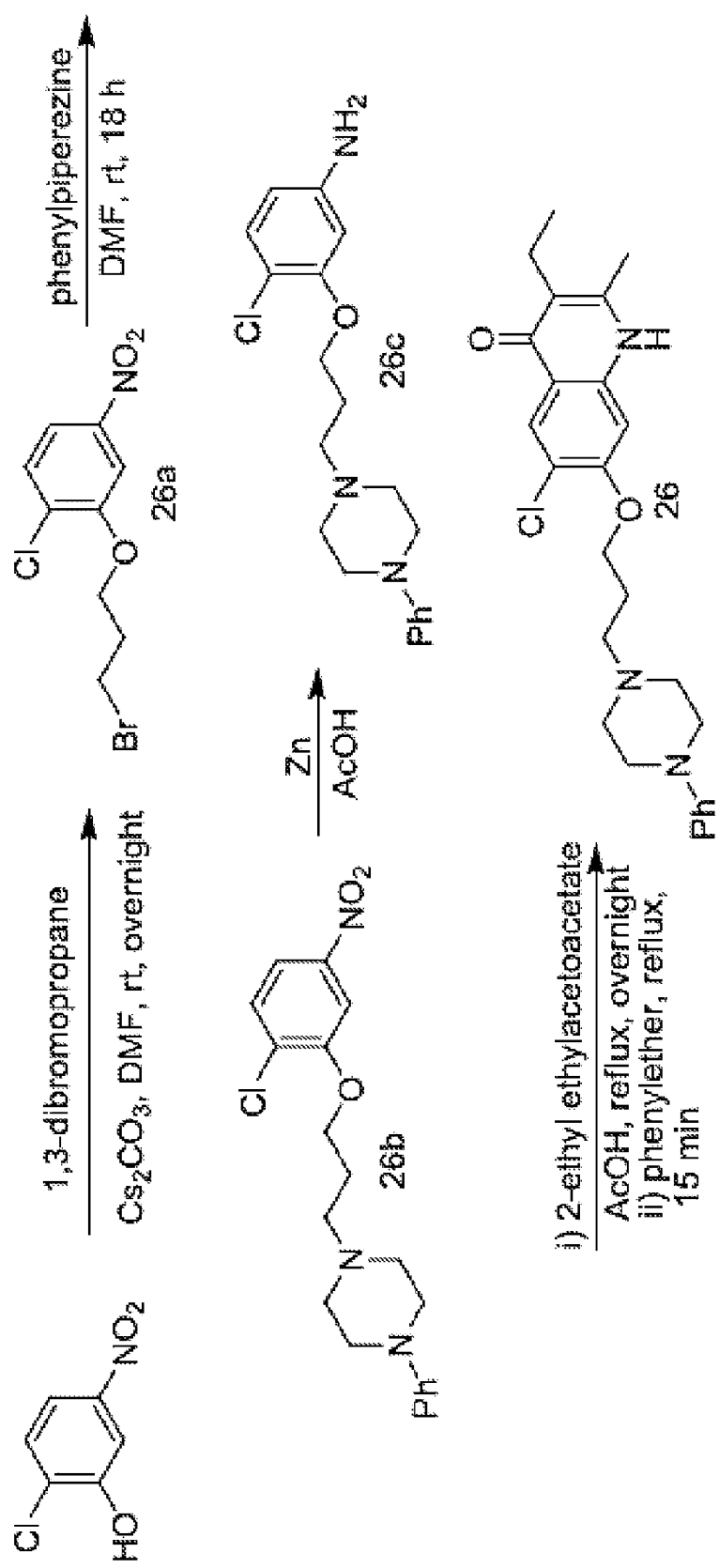
FIG. 15 schematically illustrates the synthesis of compound 26.

A library of 3-aryl PEQs (31-44) was prepared by cyclizing aniline 12 using a Conrad-Limpach protocol followed by a regioselective iodination to generate 4(1H)-quinolone, as shown in FIG. 5, which was then subjected to Suzuki-Miyaura cross-coupling conditions. The 3-halo-4(1H)-quinolone core could tolerate couplings with or without alkyl protection; however, depending on the nature of the aryl boronic acid used, higher yields were achieved starting from alkylated quinolones (Cross & Manetsch (2010) *J. Org. Chem.* 75: 8654-8657). Therefore, using O-methyl (29) or O-ethyl-3-iodo-quinoline (30), the coupling could be employed successfully followed by chemoselective dealkylation using HBr in refluxing acetic acid, as described in Reid et al., (2011) *Bioorg. Med. Chem.* 19: 513-523, incorporated herein by reference in its entirety. This dealkylation was a time-sensitive reaction and unwanted bromination or dealkylations could occur depending on the substituents of the 6- or 7-position. For example, when the 7-(2-phenoxyethoxy) group was present, a bromine could replace the phenoxy moiety when the reaction was refluxed for an extended period. A variety of boronic acids, including those containing an ortho substituent, were utilized to generate 3-arylquinolones.

Antimalarial Activity and Cytotoxicity

All synthesized quinolones were tested as described in Cross et al., (2010) *J. Med. Chem.* 53, 7076-7094 and Reid et al., (2011) *Bioorg. Med. Chem.* 19: 513-523, incorporated herein by reference in their entireties, for in vitro antimalarial activity against the clinically relevant multidrug resistant malarial strains W2 (chloroquine- and pyrimethamine-resistant) and TM90-C2B (chloroquine-, mefloquine-, pyrimethamine-, and atovaquone-resistant) and for cytotoxicity against J774 mammalian cells. Generally, the PEQs did not display signs of cytotoxicity against the mammalian cell line at less than 20 μM, rendering cytotoxicity indices ($CI=EC_{50}(J774)/EC_{50}(TM90-C2B)$) of 100 or more. These results indicate that most of the PEQs of the disclosure were selective and non-toxic agents, as shown in FIGS. 5 and 6.

The emergence of resistance and cross-resistance with atovaquone is a concern for new antimalarial compounds that target the parasite's mitochondria (e.g., atovaquone). For the structure-activity relationship study, the resistance index (RI), calculated as the ratio of the effective concentrations for TM90-C2B and W2 inhibition (RI=EC$_{50}$(TM90-C2B)/EC$_{50}$(W2)), was also determined. Compounds with an RI value of 0.3-3.0 were considered acceptable in regards to risk of cross-resistance with atovaquone, whereas compounds with an RI value greater than 10 or less than 0.1 can be considered to have clinically relevant levels of cross-resistance with atovaquone.

Structure-Activity Studies

Compound 5 was shown to have excellent activity against W2 and TM90-C2B with EC$_{50}$ values of 0.05 and 11.17 nM, respectively (FIG. 4). However, the potency difference between the two strains yielded an RI value of 223. A series of PEQs were designed, therefore, to examine the 3-, 6-, and 7-substitutents of 5 to improve potency against atovaquone-sensitive and resistant *P. falciparum*. The 6-chloro-7-methoxy analogue 15 led to a 70-fold or larger decrease in antimalarial activity for both strains, while PEQ 15 displayed a 4000-fold loss in activity for W2 compared to only a 4-fold potency decrease for TM90-C2B. Conversely, introduction of an ethyl group at the 3-position in PEQ 16 restored EC$_{50}$ values of 1.92 nM against W2 and 150 pM against TM90-C2B. The potency of 16 showed a reversed preference for TM90-C2B with an RI value of 0.08, which stands in sharp contrast to 5 that inhibits W2 approximately 220-fold more than TM90-C2B. A series of 6- and 7-substituted 2-methyl-4(1H)-quinolones containing an ethyl group in the 3-position was also prepared.

A subset was prepared to probe the role of the 6-butyl group of 16. Complete removal of the butyl group generated compound 27 with EC$_{50}$ of 104 and 71.3 nM against W2 and TM90-C2B, respectively. In comparison to 27, 6-chloro- or 6-bromo-substituted PEQs 17 and 25 displayed slightly reduced activities against W2, while their potencies for TM90-C2B were unaffected or slightly improved. PEQs 18 and 19 substituted with a methyl or a methoxy group in the 6-position were also shown to be less active against W2, but 3-fold more potent against TM90-C2B compared to 27.

A subset of 2-methyl-3-ethyl-6-chloro-substituted PEQs 20-26 were also examined, in which the group at the 7-position was varied. With the exception of methoxymethyl ether 20 and piperazine 26, all others 21-25 were 5-30 times less active against W2 and TM90-C2B in comparison to their reference compound 17. PEQs 20 and 26 were similar to 17 in potency against TM90-C2B, and approximately 4-fold less active against W2. These results indicate that the 7-(2-phenoxyethoxy) moiety greatly affects antimalarial activity and that the 3-ethyl-substituted PEQs display more favorable RI values in comparison to methyl carboxylate 5.

While retaining the 6-butyl-7-(2-phenoxyethoxy) moiety, a series of 3-aryl analogues (31-43) was prepared and tested against W2 and TM90-C2B, as shown in FIG. 6. Generally, PEQs 38-43 containing an ortho-substituted aromatic ring in the 3-position were approximately 10-fold more potent compared to the 3-aryl-substituted analogues 31-37. Ortho-substituted 3-aryl analogues 38-43 were also more potent against the W2 strain, whereas the 3-aryl PEQs 31-37 were more potent against TM90-C2B. Initially, the 3-phenyl analogue 31 was prepared, which displayed a disadvantageous EC$_{50}$ of 1072 nM against W2 and 764 nM against TM90-C2B. Next, 3-p- and 3-m-pyridyl analogues 32 and 33 were shown to have moderate activity in low micromolar or high nanomolar range.

Trifluoromethylphenyl and trifluoromethoxyphenyl substituted PEQs 34 and 35 were similar to 32 and 33 in activity. The biaryl and benzylaryl analogues 36 and 37 were inactive. Of the ortho-substituted 3-aryl analogues 38, 40, and 42 had high EC$_{50}$ against one or both strains, thereby providing reduced RI values. Fluorotrifluoromethylphenyl-substituted PEQ 35 displayed advantageous antimalarial activities with EC$_{50}$ values of 27.9 and 31.0 nM against W2 and TM90-C2B, yielding an RI value of 1.1. Analogue 43 substituted with 3,5-dimethylisoxazolyl in the 3-position was also very potent against W2 with an EC$_{50}$ of 27.0 nM and approximately 5 times less potent against TM90-C2B. Overall, though the 3-aryl series was less potent compared to 5, several analogues such as fluorotrifluoromethylphenyl-substituted PEQ 41 or isoxazole 43 showed advantageous antimalarial activity and an pharmaceutically acceptable RI value.

Accordingly, the disclosure encompasses novel PEQ analogues, including, but not limited to, a series of 29 with varying substitutions at the 2-, 3-, 6-, and 7-positions that have been assessed for antimalarial activity against the clinically relevant malarial strains TM90-C2B and W2. The most advantageous antimalarial activities were obtained when the 3-position contained an ethyl group or a fluoroaryl moiety. PEQ analogues lacking the 7-(2-phenoxyethoxy) substituent showed significant differences in EC$_{50}$ values against the two test strains. For 3-ethyl-substituted PEQs, the most advantageous activities and RI values were obtained with compounds containing a 2-phenoxyethoxy moiety in 7-position, whereas the group in the 6-position produced the activity order Bu>MeO>Me>Br>Cl>H for TM90-C2B and Bu>H>MeO>Br>Me>Cl for W2, providing a strain preference that had minor dependence on the moiety in the 6-position. Similarly, 3-aryl-substituted PEQs displaying good potencies against both strains and acceptable RI values contained the butyl in the 6-position and the 2-phenoxyethoxy group in the 7-position. Advantageous activities and acceptable RI values were obtained with PEQs 41 and 43 containing in the 3-position an ortho-substituted aromatic ring such as a fluorotrifluoromethylphenyl or a 3,5-dimethylisoxazolyl.

Pharmaceutical Formulations

It is, therefore, further contemplated for the compounds of the disclosure to be incorporated into therapeutic compositions formulated for delivering a dose or doses of the compound to an animal or human subject in need of either a therapeutic treatment for an existing malarial infection or for the prevention of an infection, and consequently in may be necessary to provide multiple doses of the effective agent until the infection has been reduced to clinically desirable levels or eliminated from the subject entirely. It is further contemplated that a single dose of the therapeutic compounds and compositions of the present disclosure may be insufficient to completely reduce the viability of the malarial parasite in an infected animal or human.

The compounds of Formulas (I) and (II) of the disclosure, pharmaceutically acceptable salts thereof, prodrugs corresponding to compounds of Formulas (I) and (II), and the pharmaceutically acceptable salts thereof, may be referred to as "active compounds." Pharmaceutical formulations comprising the active compounds of the disclosure also are provided herein. These pharmaceutical formulations may comprise active compounds as described herein and a pharmaceutically acceptable carrier. Pharmaceutical formulations can be prepared for oral, intravenous, or aerosol administration. The active compounds may have been lyophilized and that can be reconstituted to form pharmaceutically acceptable formulations for administration, for example, as by intravenous or intramuscular injection.

The therapeutically effective dosage of any compound of the disclosure, the use of which is within the scope of embodiments described herein, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level can restrict intravenous dosages to a lower level with all weights being calculated based on the weight of the active base, including the cases where a salt is employed. The duration of the treatment can be, but is not limited to, once per day for a period of two to three weeks or until the condition is essentially controlled. Treatment of a subject with lower doses and/or doses given less frequently can be used prophylactically to prevent or reduce the incidence of recurrence, e.g., a return of the infection or to prevent an infection in a subject who has never had an infection but is at risk of infection due to an increased likelihood of contact with a malarial parasite that can cause an infection. Increased likelihood for contact with a microbial agent can come from the subject being present in geographical locations where the microbial agent is known to be prevalent.

In accordance with the present methods, pharmaceutically active compounds of the disclosure can be administered orally as a solid or as a liquid, or can be administered intramuscularly or intravenously as a solution, suspension, or emulsion. Alternatively, the compounds or salts also can be administered by inhalation, intravenously, or intramuscularly as a liposomal suspension. When administered through inhalation the active compound or salt should be in the form of a plurality of solid particles or droplets having a particle size from about 0.5 to about 5 microns, and preferably from about 1 to about 2 microns.

Pharmaceutical formulations suitable for intravenous or intramuscular injection are further embodiments provided herein. The pharmaceutical formulations can comprise a compound of Formulas (I) or (II) described herein in any pharmaceutically acceptable carrier. A solution in either instance can be sterilized in a suitable manner known to those in the art, and typically by filtration through a 0.22-micron filter. Subsequent to sterilization, the solution can be dispensed into appropriate receptacles, such as depyrogenated glass vials. The dispensing is preferably done by an aseptic method. Sterilized closures can then be placed on the vials and, if desired, the vial contents can be lyophilized.

The pharmaceutical compositions of the disclosure can contain other additives, such as pH-adjusting additives. The formulations can contain antimicrobial preservatives. Useful antimicrobial preservatives include methylparaben, propylparaben, and benzyl alcohol. The antimicrobial preservative is typically employed when the formulation is placed in a vial designed for multi-dose use.

In some embodiments of the disclosure, there is provided an injectable, stable, sterile formulation comprising a compound of Formula (I) or (II) in a unit dosage form in a sealed container. The compound or salt may be provided in the form of a lyophilizate that is capable of being reconstituted with a suitable pharmaceutically acceptable carrier to form a liquid formulation suitable for injection thereof into a subject. When the compound or salt is substantially water-insoluble, a sufficient amount of emulsifying agent, which is physiologically acceptable, can be employed in sufficient quantity to emulsify the compound or salt in an aqueous carrier. One such useful emulsifying agent is phosphatidyl choline.

Accordingly, one aspect of the disclosure encompasses embodiments of a compound having the Formula I or II:

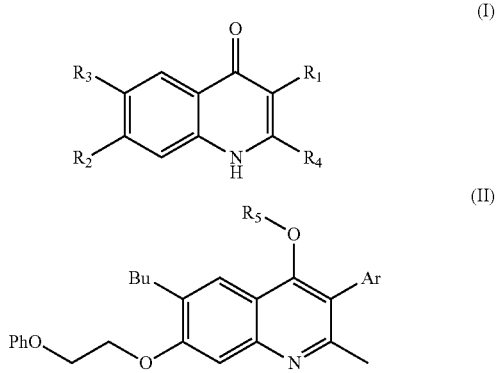

wherein, in Formula I: $R_1$ can be H, ethyl, an aryl, carboxymethyl, or a halogen; $R_2$ can be 2-phenoxyethoxy, methoxy, methoxymethoxy, 3-hydroxy-propoxy, 2-ethyl-3-oxo-butyricacid, 2-morpholino-4-yl-ethoxy-, 2-dimethylamnoethoxy, or 3-(4-phenyl-piperazin-1-yl)-propoxy; $R_3$ can be H, butyrate, a halogen, methyl, or methoxy; and $R_4$ can be H or methyl, and wherein in Formula II: $R_5$ is an H or an alkyl, and Ar is an aromatic group selected from the group consisting of: phenyl, pyridin-4-yl, pyridin-3-yl, 4-(trifluoromethyl)phenyl, 4-fluorophenoxyphenyl, 4-((4-(trifluoromethoxy)phenoxy)methyl)phenyl), (2-methyl-4-(4-(trifluoromethoxy)phenoxy)phenyl), (2-methyl-4-(trifluoromethyl)phenyl), 2,4-dimethylphenyl), (2-fluoro-4-(trifluoromethyl)phenyl), (4-chloro-2-methylphenyl), and (3,5-dimethylisooxazol-4-yl).

In some embodiments of this aspect of the disclosure, the compound can have the Formula I. In these embodiments, the compound can be selected from, but is not limited to, compounds of the group consisting of: 6-butyl-2-methyl-7-(2-phenoxyethoxy)quinolin-4(1H)-one (15), 6-butyl-3-ethyl-2-methyl-7-(2-phenoxyethoxy)quinolin-4(1H)-one (16), 6-chloro-3-ethyl-2-methyl-7-(2-phenoxy-ethoxy)-1H-quinolin-4-one (17), 3-ethyl-2,6-dimethyl-7-(2-phenoxyethoxy)-1H-quiolin-4-one (18), 3-ethyl-6-methoxy-2-methyl-7-(2-phenoxy-methoxy)-1H-quinolin-4-one (19), 6-chloro-3-ethyl-7-methoxymethoxy-2-methyl-1H-quinoline-4-one (20), 6-chloro-3-ethyl-7-(3-hydroxy-propoxy)-2-methyl-1H-quinolin-4-one (21), 2-ethyl-3-oxo-butyricacid-3-(6-chloro-3-ethyl-2-methyl-4-oxo-1,4-dihydro-quinolin-7-yloxy)-propyl ester (22), 6-chloro-3-ethyl-2-methyl-7-(2-morpholin-4-yl-ethoxy)-1H-quinolin-4-one (23), 6-chloro-7-(2-dimethylamino-ethoxy)-3-ethyl-2-methyl-1H-quinolin-4-one (24), 6-bromo-3-ethyl-2-methyl-7-(2-phenoxy-ethoxy)-1H-quinolin-4-one (25), and 6-chloro-3-ethyl-2-methyl-7-[3-(4-phenyl-piperazin-1-yl)-propoxy]-1H-quinolin-4-one (26).

In other embodiments of this aspect of the disclosure, the compound can have Formula II. In these embodiments, $R_5$ can be methyl or ethyl and the compound can be selected from, but is not limited to, compounds of the group consisting of: 6-butyl-2-methyl-7-(2-phenoxyethoxy)-3-phenylquinolin-4(1H)-one (31), 6-butyl-2-methyl-7-(2-phenoxyethoxy)-3-(pyridin-4-yl)quinolin-4(1H)-one (32), 6-butyl-2-methyl-7-(2-phenoxyethoxy)-3-(pyridin-3-yl)quinolin-4(1H)-one (33), 6-butyl-2-methyl-7-(2-phenoxyethoxy)-3-(4-(trifluoromethyl)phenyl)quinolin-4(1H)-one (34), 6-butyl-2-methyl-7-(2-phenoxyethoxy)-3-(4-(trifluoromethoxy)phenyl)quinolin-4(1H)-one (35), 6-butyl-3-(3-(4-fluorophenoxy)phenyl)-2-methyl-7-(2-phenoxyethoxy)quinolin-4(1H)-one (36), 6-butyl-2-methyl-7-(2-phenoxyethoxy)-3-(4-((4-(trifluoromethoxy)phenoxy)methyl)phenyl)quinolin-4(1H)-one (37), 6-butyl-2-methyl-3-(2-methyl-4-(4-(trifluoromethoxy)phenoxy)phenyl)-7-(2-phenoxyethoxy)-quinolin-4(1H)-one (38), 6-butyl-2-methyl-3-(2-methyl-4-(trifluoromethyl)phenyl)-7-(2-phenoxyethoxy)quinolin-4(1H)-one (39), 6-butyl-3-(2,4-dimethylphenyl)-2-methyl-7-(2-phenoxyethoxy)quinolin-4(1H)-one (40), 6-butyl-3-(2-fluoro-4-(trifluoromethyl)phenyl)-2-methyl-7-(2-phenoxyethoxy)quinolin-4(1H)-one (41), 6-butyl-3-(4-chloro-2-methylphenyl)-2-methyl-7-(2-phenoxyethoxy)quinolin-4(1H)-one (42), and 6-butyl-3-(3,5-dimethylisoxazol-4-yl)-2-methyl-7-(2-phenoxyethoxy)quinolin-4(1H)-one (43).

Another aspect of the disclosure encompasses embodiments of a pharmaceutically acceptable composition comprising a therapeutic amount of a compound selected from the group consisting of: 6-butyl-2-methyl-7-(2-phenoxyethoxy)quinolin-4(1H)-one (15), 6-butyl-3-ethyl-2-methyl-7-(2-phenoxyethoxy)quinolin-4(1H)-one (16), 6-chloro-3-ethyl-2-methyl-7-(2-phenoxy-ethoxy)-1H-quinolin-4-one (17), 3-ethyl-2,6-dimethyl-7-(2-phenoxy-ethoxy)-1H-quiolin-4-one (18), 3-ethyl-6-methoxy-2-methyl-7-(2-phenoxy-methoxy)-1H-quinolin-4-one (19), 6-chloro-3-ethyl-7-methoxymethoxy-2-methyl-1H-quinoline-4-one (20), 6-chloro-3-ethyl-7-(3-hydroxy-propoxy)-2-methyl-1H-quinolin-4-one (21), 2-ethyl-3-oxo-butyricacid-3-(6-chloro-3-ethyl-2-methyl-4-oxo-1,4-dihydro-quinolin-7-yloxy)-propyl ester (22), 6-chloro-3-ethyl-2-methyl-7-(2-morpholin-4-yl-ethoxy)-1H-quinolin-4-one (23), 6-chloro-7-(2-dimethylamino-ethoxy)-3-ethyl-2-methyl-1H-quinolin-4-one (24), 6-bromo-3-ethyl-2-methyl-7-(2-phenoxy-ethoxy)-1H-quinolin-4-one (25), 6-chloro-3-ethyl-2-methyl-7-[3-(4-phenyl-piperazin-1-yl)-propoxy]-1H-quinolin-4-one (26), 6-butyl-2-methyl-7-(2-phenoxyethoxy)-3-phenylquinolin-4(1H)-one (31), 6-butyl-2-methyl-7-(2-phenoxyethoxy)-3-(pyridin-4-yl)quinolin-4(1H)-one (32), 6-butyl-2-methyl-7-(2-phenoxyethoxy)-3-(pyridin-3-yl)quinolin-4(1H)-one (33), 6-butyl-2-methyl-7-(2-phenoxyethoxy)-3-(4-(trifluoromethyl)phenyl)quinolin-4(1H)-one (34), 6-butyl-2-methyl-7-(2-phenoxyethoxy)-3-(4-(trifluoromethoxy)phenyl)quinolin-4(1H)-one (35), 6-butyl-3-(3-(4-fluorophenoxy)phenyl)-2-methyl-7-(2-phenoxyethoxy)quinolin-4(1H)-one (36), 6-butyl-2-methyl-7-(2-phenoxyethoxy)-3-(4-((4-(trifluoromethoxy)phenoxy)methyl)phenyl)quinolin-4(1H)-one (37), 6-butyl-2-methyl-3-(2-methyl-4-(4-(trifluoromethoxy)phenoxy)phenyl)-7-(2-phenoxyethoxy)-quinolin-4(1H)-one (38), 6-butyl-2-methyl-3-(2-methyl-4-(trifluoromethyl)phenyl)-7-(2-phenoxyethoxy)quinolin-4(1H)-one (39), 6-butyl-3-(2,4-dimethylphenyl)-2-methyl-7-(2-phenoxyethoxy)quinolin-4(1H)-one (40), 6-butyl-3-(2-fluoro-4-(trifluoromethyl)phenyl)-2-methyl-7-(2-phenoxyethoxy)quinolin-4(1H)-one (41), 6-butyl-3-(4-chloro-2-methylphenyl)-2-methyl-7-(2-phenoxyethoxy)quinolin-4(1H)-one (42), and 6-butyl-3-(3,5-dimethylisoxazol-4-yl)-2-methyl-7-(2-phenoxyethoxy)quinolin-4(1H)-one (43) that when administered to a recipient animal or human subject as a single dose or as multiple doses is effective in reducing or preventing a malarial infection in the subject.

In this aspect of the disclosure, the embodiments can further comprise a pharmaceutically acceptable composition of claim 6, further comprising a pharmaceutically acceptable carrier.

Yet another aspect of the disclosure encompasses a method of reducing the viability of a population of malarial parasites, the method comprising administering to an animal or human subject a therapeutically effective amount of a pharmaceutically acceptable composition comprising a compound selected from the group consisting of: 6-butyl-2-methyl-7-(2-phenoxyethoxy)quinolin-4(1H)-one (15), 6-butyl-3-ethyl-2-methyl-7-(2-phenoxyethoxy)quinolin-4(1H)-one (16), 6-chloro-3-ethyl-2-methyl-7-(2-phenoxy-ethoxy)-1H-quinolin-4-one (17), 3-ethyl-2,6-dimethyl-7-(2-phenoxy-ethoxy)-1H-quiolin-4-one (18), 3-ethyl-6-methoxy-2-methyl-7-(2-phenoxy-methoxy)-1H-quinolin-4-one (19), 6-chloro-3-ethyl-7-methoxymethoxy-2-methyl-1H-quinoline-4-one (20), 6-chloro-3-ethyl-7-(3-hydroxy-propoxy)-2-methyl-1H-quinolin-4-one (21), 2-ethyl-3-oxo-butyricacid-3-(6-chloro-3-ethyl-2-methyl-4-oxo-1,4-dihydro-quinolin-7-yloxy)-propyl ester (22), 6-chloro-3-ethyl-2-methyl-7-(2-morpholin-4-yl-ethoxy)-1H-quinolin-4-one (23), 6-chloro-7-(2-dimethylamino-ethoxy)-3-ethyl-2-methyl-1H-quinolin-4-one (24), 6-bromo-3-ethyl-2-methyl-7-(2-phenoxy-ethoxy)-1H-quinolin-4-one (25), and 6-chloro-3-ethyl-2-methyl-7-[3-(4-phenyl-piperazin-1-yl)-propoxy]-1H-quinolin-4-one (26).

In some embodiments of this aspect of the disclosure, the compound can be selected from the group consisting of: 6-butyl-2-methyl-7-(2-phenoxyethoxy)-3-phenylquinolin-4(1H)-one (31), 6-butyl-2-methyl-7-(2-phenoxyethoxy)-3-(pyridin-4-yl)quinolin-4(1H)-one (32), 6-butyl-2-methyl-7-(2-phenoxyethoxy)-3-(pyridin-3-yl)quinolin-4(1H)-one (33), 6-butyl-2-methyl-7-(2-phenoxyethoxy)-3-(4-(trifluoromethyl)phenyl)quinolin-4(1H)-one (34), 6-butyl-2-methyl-7-(2-phenoxyethoxy)-3-(4-(trifluoromethoxy)phenyl)

quinolin-4(1H)-one (35), 6-butyl-3-(3-(4-fluorophenoxy)phenyl)-2-methyl-7-(2-phenoxyethoxy)quinolin-4(1H)-one (36), 6-butyl-2-methyl-7-(2-phenoxyethoxy)-3-(4-((4-(trifluoromethoxy)phenoxy)methyl)phenyl)quinolin-4(1H)-one (37), 6-butyl-2-methyl-3-(2-methyl-4-(4-(trifluoromethoxy)phenoxy)phenyl)-7-(2-phenoxyethoxy)quinolin-4(1H)-one (38), 6-butyl-2-methyl-3-(2-methyl-4-(trifluoromethyl)phenyl)-7-(2-phenoxyethoxy)quinolin-4(1H)-one (39), 6-butyl-3-(2,4-dimethylphenyl)-2-methyl-7-(2-phenoxyethoxy)quinolin-4(1H)-one (40), 6-butyl-3-(2-fluoro-4-(trifluoromethyl)phenyl)-2-methyl-7-(2-phenoxyethoxy)quinolin-4(1H)-one (41), 6-butyl-3-(4-chloro-2-methylphenyl)-2-methyl-7-(2-phenoxyethoxy)quinolin-4(1H)-one (42), and 6-butyl-3-(3,5-dimethylisoxazol-4-yl)-2-methyl-7-(2-phenoxyethoxy)quinolin-4(1H)-one (43).

Additional embodiments provided herein include liposomal formulations of the compounds disclosed herein. The technology for forming liposomal suspensions is well known in the art.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

The identity of all title compounds was verified via $^1$H NMR, $^{13}$C NMR, and HPLC/HRMS. The chemical purity of the titled compounds was determined using the following conditions: an Agilent 1100 series LC/MSD with a Eclipse XDB-C18 (4.6 mm×100 mm, 5 µm) reversed phase column; method: 10% (v/v) of acetonitrile (+0.05% TFA) in 90% (v/v) of $H_2O$ (+0.05% TFA), ramped to 100% acetonitrile (+0.05% TFA) over 9 min, and holding at 100% acetonitrile for 4 min. with a flow rate of 0.7 mL/min, UV detector, 254 nm.

The purity of each compound was greater than or equal to 95% in this analysis. NMR spectra were recorded at ambient temperature on a 400 or 500 MHz Varian NMR spectrometer in the solvent indicated. All $^1$H NMR experiments are reported in units, parts per million (ppm) downfield of TMS and were measured relative to the signals for chloroform (7.26 ppm) and dimethylsulfoxide (2.50 ppm). All $^{13}$C NMR spectra were reported in ppm relative to the signals for chloroform (77 ppm) and dimethylsulfoxide (39.5 ppm) with $^1$H decoupled observation. Data for $^1$H NMR are reported as follows: chemical shift (δ ppm), multiplicity (s=singlet, d=doublet, t=triplet, q=quartet, m=multiplet), integration and coupling constant (Hz), whereas $^{13}$CNMR analyses were obtained at 101 MHz and reported in terms of chemical shift. NMR data was analyzed by using MestReNova Software ver. 5.3.2-4936. High resolution mass spectra (HRMS) were performed on an Agilent LC/MSD TOF system G3250AA. Silicycle silica gel 230-400 (particle size 40-63 µm) mesh was used for all flash column chromatography.

Example 2

General Procedure A: Preparation of 3-substituted 2-methylquinolin-4(1H)-ones: 4(1H)-quinolones were prepared by using one of the standard procedures for Conrad-Limpach reaction. An oven-dry 100 mL rbf attached to a Dean-Stark trap equipped with a reflux condenser was charged with an aniline (0.025 mol), corresponded ethyl acetoacetate (0.25-0.05 mol), benzene (25 mL) and glacial acidic acid (1 mL). The mixture was heated at 100° C. until no more water was separated (3-24 hrs). The benzene was distilled under the reduced pressure and resulting enamine was then used in the next step without further purification. Biphenyl ether (30 mL) was stirred and heated at reflux while enamine was added rapidly through the dropping funnel. Stirring and refluxing continued for 10-15 mins until no more ethanol separates within the Dean-Stark trap. The mixture was then allowed to cool down to room temperature while precipitation arises. The solid was filtered off and washed with hexane and acetone. Ice cold methanol washing may be necessary in some cases. The solid was typically recrystallized with DMF if necessary.

Example 3

General Procedure B: Halogenation of substituted 2-methylquinolin-4(1H)-one: The halogenation was done following a similar procedure reported by Renault et al. Thus 5 eq. of iodine was added dropwise to a stirred solution or slurry of 2-methylquinolin-4(1H)-one in 2 M solution of sodium hydroxide and methanol (approximately 1:1) at room temperature. Stirring was continued until LCMS indicates absence of starting material (3-24 hrs). In some cases more than 8 eq of iodine was required. The mixture was then acidified with acetic acid; precipitate was collected by filtration, washed with water, and recrystallized from DMF.

Example 4

General Procedure C: Alkylation of 2-methylquinolin-4 (1H)-one: To a flame dried-backfilled round bottom flask was added quinolone (0.72 g, 2.8 mmol) and cesium carbonate (1.37 g, 4.2 mmol). DMF (14.5 mL) was added and this slurry was allowed to stir at room temperature for 1 hr. Next, iodomethane (0.88 mL, 14 mmol) was added dropwise and the reaction left until completion was observed via HPLC analysis. The reaction was then poured onto water (20 mL) and diluted with chloroform (20 mL). The organic layer was then washed twice with water (20 mL) followed by brine (20 mL). The organic layer was then dried over sodium sulfate and concentrated in vacuo. The crude compound was columned via flash chromatography (Hexane/ethyl acetate gradient).

Example 5

General Procedure D: Suzuki-Coupling of 3-iodo-2-methylquinolin-4(1H)-one: An oven-dried Schlenk tube was flame-dried and backfilled with argon (×3). The tube was charged with 4(1H)-quinolone (100 mg, 0.4 mmol), $Pd_2(dba)_3$ (14.5 mg, 0.016 mmol), SPhos (13 mg, 0.032 mmol), boronic acid (97 mg, 0.6 mmol), and anhydrous powdered potassium phosphate (168 mg, 0.79 mmol). The Schlenk tube was fitted with a rubber septum and evacuated and backfilled with argon (this process was repeated three times).

Dry solvent (Toluene, DMF, or 2-butanol, 3 mL) was added through the septum via syringe and the resulting solution was stirred for 1 min. while purging with argon before replacing the rubber septum with the Teflon screwcap. The reaction was set to the oil bath until completion was observed via HPLC analysis. The reaction was cooled to room temperature and then diluted with 20 mL chloroform and 20 mL of methanol. This mixture was brought to a boil with a heat gun and then filtered over a pad of celite. The eluent was concentrated under reduced pressure and the residual oil was purified further via flash chromatography.

Example 6

General Procedure E: Suzuki-Coupling of 3-iodo-2-methylquinolin-4(1H)-one: An oven-dried microwave reactor tube was flame-dried and backfilled with argon (×3). The tube was then charged with 4(1H)-quinolone (125 mg, 0.26 mmol), $Pd_2(dba)_3$ (3.5 mg, 0.004 mmol), $SP_{hos}$ (3.2 mg, 0.008 mmol), boronic acid (52 mg, 0.39 mmol). The Schlenk tube was fitted with a rubber septum and then evacuated and backfilled with argon (this process was repeated three times).

Dry DMF 5 mL and 1M sodium carbonate 1 mL was added through the septum via syringe and the resulting solution was placed in a microwave reactor for 20 mins at 140° C. The reaction was monitored via HPLC analysis. The reaction was cooled to room temperature and diluted with 2 mL chloroform and 2 mL of methanol. This mixture was brought to a boil with a heat gun and then filtered over a pad of celite. The eluent was concentrated under reduced pressure and the residual oil was purified further via flash chromatography.

Example 7

General Procedure F: Suzuki-Coupling of 6-butyl-4-ethoxy-3-iodo-2-methyl-7-(2-phenoxyethoxy)quinoline: An oven-dried Schlenk tube was flame-dried and backfilled with argon (×3). The tube was then charged with 6-butyl-4-ethoxy-3-iodo-2-methyl-7-(2-phenoxyethoxy)quinoline (100 mg, 0.4 mmol), $Pd_2(dba)_3$ (14.5 mg, 0.016 mmol), $SP_{hos}$ (13 mg, 0.032 mmol), boronic acid (97 mg, 0.6 mmol), and anhydrous powdered $K_3PO_4$ (168 mg, 0.79 mmol). The Schlenk tube was fitted with a rubber septum and then evacuated and backfilled with argon (this process was repeated three times).

Dry solvent (Toluene, DMF, or 2-butanol, 3 mL) was added through the septum via syringe and the resulting solution was stirred for 1 min. while purging with argon before replacing the rubber septum with the Teflon screwcap. The reaction was set to the oil bath until completion was observed via HPLC analysis. The reaction was cooled to room temperature and then diluted with 20 mL chloroform and 20 mL of methanol. This mixture was brought to a boil with a heat gun and then filtered over a pad of celite. The eluent was concentrated under reduced pressure and the residual oil was purified further via flash chromatography.

Example 8

General Procedure G: O-ethyl Hydrolysis: 6-Butyl-4-methoxy-2-methyl-7-(2-phenoxyethoxy)-3-phenylquinoline (100 mg, 0.226 mmol) was dissolved in 1 mL of acetic acid and 1 mL of HBr. The reaction was refluxed for 1.5 hrs. and checked via LC-MS to determine completion. Upon completion, the reaction was poured onto ice and water and filtered. The solid was then dried in an oven for 1 hrs. and recrystallized from DMF.

Example 9

General Procedure H: Alkylation of Acyl Aniline: The mixture of phenol (700 mg, 3.78 mmol), β-bromophenetole (836 mg, 4.16 mmol) and cesium carbonate (1.838 mg, 5.67 mmol) in DMF (8 mL) was stirred overnight at 50° C. The reaction mixture was diluted with water (10 mL) and extracted with ethyl acetate (3×20 mL). The combined extracts were dried over sodium sulfate and purified by recrystallization or flash chromatography.

Example 10

General Procedure I: Hydrolysis of Acetamide: N-(4-Chloro-3-(methoxymethoxy)phenyl)acetamide (700 mg, 3.05 mmol) and KOH (2.39 g, 42.8 mmol) was added to a flame-dried flask and subsequently dissolved in 10 mL of 9:1 ethanol:water solution. The mixture was refluxed overnight. The ethanol was concentrated in vacuo, diluted with water (5 mL) and extracted with ethyl acetate (3×20 mL). The combined extracts were dried over sodium sulfate and purified by flash column chromatography to get the product (0.480 g) in 84% yield.

Example 11

J774 Cytotoxicity Assay: Mouse macrophage cell line J774 was cultured in RPMI-1640 media with phenol-red containing L-glutamine supplemented with 10% fetal bovine serum, penicillin (50 Units/mL) and streptomycin (50 µg/mL). For seeding into 96 well plates the J774 cells were diluted to $5 \times 10^5$ cells/mL. Cells were dispensed into 96 well plates at a volume of 100 µL/well giving a final concentration of $5 \times 10^4$ cells/well. Plates were incubated for 24 hrs. at 37° C. and 5% $CO_2$ to allow the attachment of J774 to the bottom of the plate wells. Test compounds were prepared by diluting to 10 µg/mL or 20 nM followed by 1:2 serial dilutions over 11 concentrations. After 24 hrs. the media was removed from the wells and serially diluted test compounds were added to each well. Positive and negative control wells were included on each assay plate. Plates containing cells and test compounds were then incubated for 72 hrs. at 37° C. and 5% $CO_2$. Cell proliferation was assessed using CellTiter 96 Aqueous One Solution Cell Proliferation Assay reagent (Promega). To each well 20 µL of reagent was added followed by incubation for 4 hrs. at 37° C. and 5% $CO_2$. A Spectramax M2e (Molecular Devices) plate reader was used to read absorbance at 490 nM. $IC_{50}$ values were determined using a custom database manager (Dataspects, Inc.). Nonlinear regression analysis was used to calculate $IC_{50}$ values.

Example 12

Parasite Culturing: *P. falciparum* clone W2/Indochina and TM90C2B/Thailand were grown in continuous culture using RPMI 1640 media containing 10% heat-inactivated type A+ human plasma, sodium bicarbonate (2.4 g/L), HEPES (5.94 g/L) and 4% washed human type A+ erythrocytes. Cultures were gassed with a 90% nitrogen, 5% oxygen and 5% carbon dioxide mixture followed by incubation at 37° C.

Example 13

Assay Preparation: Test compounds at 5 mg/mL in DMSO were diluted at least 1:400 and then serially diluted in duplicate over 11 concentrations. *P. falciparum* cultures with greater than 70% ring stage parasites were diluted to 0.5-0.7% parasitemia and 1.5% hematocrit in RPMI 1640 media. In 96-well plates a volume of 90 μl/well of parasitized erythrocytes was added on top of 10 μL/well of the test compound. A separate plate containing chloroquine, dihydroartemisinin and atovaquone was added to each set of assay plates as control drugs. A Beckman Coulter Biomek 3000 was used to dispense test compounds, control drugs and parasitized erythrocytes into the microtiter plates. Positive and negative controls were included in each plate. Positive controls consisted of drug-free parasitized erythrocytes and negative controls consisted of parasitized erythrocytes dosed with a high concentration of chloroquine or dihydroartemisinin that ensured 100% parasite death. Assay plates were placed into a plastic gassing chamber and equilibrated with 90% nitrogen, 5% oxygen and 5% carbon dioxide mixture then incubated at 37° C. for 72 hrs. The assay plates were then frozen at −80° C. until later processed for parasite growth determinations.

Example 14

SYBR Green I Processing: Assay plates were removed from −80° C. storage and allowed to thaw at room temperature. Using the Beckman Biomek 3000, 100 μL was transferred from the assay plates into 96-well black assay plates. Next, 100 μl of SYBR green I (Invitrogen) in 2× lysis buffer (0.2 μl SYBR green I/mL of 2× lysis buffer (0.008% saponin, 0.08% Triton X-100, 20 mM Tris and 5 mM EDTA)) was dispensed into each well of the 96-well black assay plate using the Beckman Coulter Biomek 3000. Upon addition of SYBR green I the microtiter plates were incubated for 1 hrs. in the dark. Relative Fluorescence units (RFU) were read using a Molecular Devices Spectramax microplate reader.

Example 15

Data Analysis: Data analysis was performed using a custom database manager (Dataspects, Inc). Nonlinear regression analysis was used to calculate $EC_{50}$.

Example 16

Compound Characterization: Methyl 6-butyl-2-methyl-4-oxo-7-(2-phenoxyethoxy)-1,4-dihydroquinoline-3-carboxylate (5): $^1$H NMR (400 MHz, DMSO) δ 12.10 (s, 1H), 8.48 (s, 1H), 7.87 (s, 1H), 7.31 (t, J=8.0 Hz, 2H), 7.05 (s, 15H), 6.98 (dd, J=12.5, 7.7 Hz, 3H), 4.40 (s, 4H), 3.72 (s, 3H), 2.61 (t, J=7.5 Hz, 2H), 1.52 (dd, J=15.1, 7.9 Hz, 2H), 1.27-1.21 (m, 2H), 0.84 (t, J=7.3 Hz, 3H). HRMS (ESI) calculated for $C_{23}H_{25}NO_5$ [M+H]$^+$: 396.1805. found 396.1800.

Example 17

3-acetamidophenyl butyrate (7): N-(3-Hydroxyphenyl)acetamide (300 g) was stirred in pyridine (990 mL) followed by the addition of butyryl chloride (246 mL). This reaction was stirred at room temperature for 30 min. The resulting crystalline suspension was left for 18 hrs. to ensure completion. The mixture was dissolved in water and ethyl acetate (1:1, 1000 mL), the organic layer was separated and washed with brine (3×1000 mL). The organic layer was dried over sodium sulfate and concentrated in vacuo at 70° C. to remove pyridine. Upon cooling the oil become a very low melting solid. This solid was carefully added to a coarse 500 mL frit and dried. Minimal washing with ice cold hexane was used to cake the solid. The final compound was collected to provide the title compound in 75% yield (440 g) as a light-yellow solid.
$^1$H NMR (250 MHz, CDCl$_3$) δ 7.92 (s, 1H), 7.37 (s, 1H), 7.17 (d, J=8.1 Hz, 1H), 7.03 (d, J=7.5 Hz, 1H), 6.70 (d, J=7.8 Hz, 1H), 2.46 (t, J=7.4 Hz, 2H), 1.96 (s, 3H), 1.70 (dd, J=14.7, 7.4 Hz, 2H), 0.96 (t, J=7.4 Hz, 3H).

Example 18

N-(4-butyryl-3-hydroxyphenyl)acetamide (8): 3-Acetamidophenyl butyrate (440 g, 1.98 mol) was added to a 2-neck 1-L round bottom flask. Finely mortared aluminum chloride (560 g, 4.15 mol) was added to the flask and the two solids were heated to approximately 150° C. at which point a glassy brittle solid formed. This process was extremely exothermic and a large amount of HCl gas was formed. This solid was removed from the reaction flask and re-mortared into a very fine orange powder. This powder was then re-heated at 175° C. overnight. Upon cooling the solid was added to 2NH$_2$SO$_4$ and ice and stirred for several hours. The solid was then filtered off and washed liberally with water. Next, 1M NaOH was used to dissolve the solid completely, followed by acidification of this solution with acetic acid. This resulting solid was filtered and recrystallized with benzene to obtain the title compound in 75% yield (330 g).
$^1$H NMR (500 MHz, CDCl$_3$) δ 12.66 (s, 1H), 8.12 (s, 1H), 7.70 (d, J=8.8 Hz, 1H), 7.17 (d, J=8.8 Hz, 1H), 7.13 (s, 1H), 2.90 (t, J=7.4 Hz, 2H), 2.21 (s, 3H), 1.77 (dt, J=14.8, 7.4 Hz, 2H), 1.02 (t, J=7.4 Hz, 3H).
$^{13}$C NMR (126 MHz, CDCl$_3$) δ 205.51, 169.15, 163.75, 144.90, 131.35, 115.73, 110.35, 107.37, 39.89, 24.81, 18.12, 13.85.

Example 19

N-(3-hydroxy-4-(1-hydroxybutyl)phenyl)acetamide (9): N-(4-Butyryl-3-hydroxyphenyl)acetamido (330 g, 1.48 mol) was dissolved in 2 L of DCM and 1 L of MeOH. This solution was chilled to 0° C. and sodium borotetrahydride (33 g, 0.87 mol) was added portion-wise over 30 mins. Upon completion by TLC the reaction was quenched by the slow addition of ice. The resulting mixture was slowly evaporated to remove the methanol. The resulting solution was taken up in 1 L of ethyl acetate and washed with 1M HCl. The organic layer was then washed three times with water and once with brine. The organic layer was dried over sodium sulfate and concentrated in vacuo to give a brown viscous oil. This oil was exhaustively columned on a 1 L column and eluted with ethyl acetate:hexane (2:1) over the course of approximately 12 column loads to obtain the title compound in 56% yield (184 g).

Example 20

N-(4-butyl-3-hydroxyphenyl)acetamide (10): N-(3-Hydroxy-4-(1-hydroxybutyl)phenyl)acetamide (184 g) was reduced in 20 g batches by dissolving it in de-oxygenated acetic acid (210 mL) in the presence of 10% Pd/C (7 g) at 60 Psi in a Parr hydrogenator for eleven hrs. Upon completion the reaction was filtered over celite and diluted. The acetic acid was removed in vacuo. The resulting oil was diluted with ethyl acetate and was washed three times with water and once with brine. The organic layer was dried over sodium sulfate and concentrated in vacuo. The crude compound was purified via flash chromatography with 100% ethyl acetate to obtain the title compound in 70% yield (120 g) as a waxy tan solid.

Example 21

N-(4-butyl-3-(2-phenoxyethoxy)phenyl)acetamide (11): To a flame dried flask back-filled with argon (×2) was added sodium hydride (26.5 g, 1.1 mol) and 325 mL of anhydrous DMF. A solution of N-(4-butyl-3-hydroxyphenyl)acetamide (120 g, 0.58 mol) dissolved in 325 mL of anhydrous DMF was added via dropping funnel over 30 min. at 0° C. The reaction was then brought to 75° C. and held for 4 hrs. Upon completion the reaction was cooled to room temperature and filtered over celite. The resulting solution was diluted with ethyl acetate (600 mL) and washed three times with ice-cold water and once with brine. The organic layer was dried over sodium sulfate and concentrated in vacuo. The crude oil was purified further via flash chromatography with hexane:ethyl acetate (2:1) to obtain the title compound in 71% yield (132 g) as a light brown solid.

Example 22

4-butyl-3-(2-phenoxyethoxy)aniline (12): N-(4-Butyl-3-(2-phenoxyethoxy)phenyl)acetamide (132 g, 0.41 mol) was dissolved in ethanol (897 mL) and water (104 mL). KOH (312 g, 5.57 mol) was added at 0° C. and the solution was allowed to reflux for 18 hrs. Upon completion the reaction was cooled to room temperature and diluted with 2 L of water and 2 L of DCM. The organic layer was washed with water (×2) and dried over sodium sulfate. The crude compound was purified further via flash chromatography with hexane:ethyl acetate (1:1) to obtain the title compound in 80% yield (92 g) as a pink solid.

Example 23

4-chloro-3-methoxyaniline (13): 900 mL of ammonia was condensed at −78° C. 1 g of thinly shaven strips of sodium was added followed by 1.0 g of iron (III) nitrate nonahydrate. Upon disappearance of the deep blue color 25 g of thinly shaven strips of sodium was added. After 30 mins of stirring at −78° C., 50 g of 2,5-dichloroanisole was added as a solution in hexane (70 mL) dropwise and the reaction warmed to −45° C. for 2 hrs. Upon completion the ammonia was allowed to evaporate. The crude pot was then diluted in chloroform and 100 g of $NH_4Cl$ was added slowly. The combines were taken up in a separatory funnel and washed with water (3×) followed by brine (1×). The organic layer was dried over sodium sulfate and concentrated in vacuo. The resulting solid can be used without further purification. Yield: 99%.

$^1$H NMR (400 MHz, DMSO) δ 6.98 (d, J=8.4, 1H), 6.34 (d, J=1.8, 1H), 6.16 (dd, J=8.4, 1.9, 1H), 5.23 (s, 2H), 3.74 (s, 3H).

$^{13}$C NMR (101 MHz, DMSO) δ 154.90, 149.16, 129.68, 107.02, 106.74, 98.66, 55.38. HRMS (ESI) calculated for $C_7H_8ClNO$ [M+H]$^+$: 157.0367. found: 157.0361.

Example 24

6-butyl-2-methyl-7-(2-phenoxyethoxy)quinolin-4(1H)-one (15): $^1$H NMR (400 MHz, DMSO) δ 11.35 (s, 1H), 7.74 (s, 1H), 7.31 (t, J=7.8 Hz, 2H), 7.05-6.87 (m, 4H), 5.79 (s, 1H), 4.38 (d, J=6.7 Hz, 4H), 2.58 (t, J=7.4 Hz, 2H), 2.29 (s, 3H), 1.58-1.47 (m, 2H), 1.25 (dd, J=14.6, 7.3 Hz, 2H), 0.83 (t, J=7.3 Hz, 3H).

$^{13}$C NMR (101 MHz, DMSO) δ 176.87, 159.75, 159.09, 149.21, 140.85, 130.18, 127.88, 125.94, 121.45, 119.12, 115.23, 108.68, 98.82, 67.50, 66.77, 32.03, 29.87, 22.51, 20.02, 14.42. HRMS (ESI) calculated for $C_{22}H_{25}NO_3$ [M+H]$^+$: 352.1907. found 352.1900.

Example 25

6-butyl-3-ethyl-2-methyl-7-(2-phenoxyethoxy)quinolin-4 (1H)-one (16): $^1$H NMR (400 MHz, DMSO) δ 11.15 (s, 1H), 7.76 (s, 1H), 7.31 (t, J=7.9 Hz, 2H), 7.02-6.93 (m, 3H), 6.87 (s, 1H), 4.38 (d, J=9.8 Hz, 4H), 2.58 (t, J=7.4 Hz, 2H), 2.49-2.43 (m, 2H), 2.34 (s, 3H), 1.51 (dd, J=14.8, 7.5 Hz, 2H), 1.25 (dd, J=14.7, 7.3 Hz, 2H), 0.98 (t, J=7.3 Hz, 3H), 0.83 (t, J=7.3 Hz, 3H).

$^{13}$C NMR (101 MHz, DMSO) δ 175.53, 159.43, 159.10, 145.05, 139.87, 130.67, 130.16, 127.57, 126.24, 121.43, 120.52, 119.25, 118.23, 115.22, 98.32, 67.42, 66.78, 32.09, 29.92, 22.50, 18.59, 17.86, 14.42.

Example 26

Synthesis of compound (17)

N-(4-chloro-3-hydroxyphenyl)acetamide (17a): Acetic anhydride (3.0 mL, 42.0 mmol) was added to a solution of 4-chloro-3-hydroxy aniline (4.0 g, 28 mmol) in acetic acid (20 mL), and the reaction was refluxed for 5 mins. The reaction mixture was cooled to room temperature and the product was solidified. It was filtered off and washed with water (10 mL) and dried to obtain the product 17a in 93% yield (4.8 g) as a creamy white solid. There was no need for further purification.

$^1$H NMR (400 MHz, Acetone) δ 9.26 (br s, 1H), 9.01 (s, 1H), 7.72 (d, J=2.4 Hz, 1H), 7.20 (d, J=8.6 Hz, 1H), 6.93 (dd, J=8.6, 2.4 Hz, 1H), 2.09 (s, 3H).

$^{13}$C NMR (101 MHz, Acetone) δ 169.66, 154.05, 140.20, 130.49, 115.18, 112.16, 108.56, 24.35. HRMS (ESI) calculated for $C_8H_8ClNO_2$ [M+Na]$^+$: 208.0136. Found: 208.0144.

N-[4-chloro-3-(2-phenoxy-ethoxy)-phenyl]-acetamide (17b): The compound 17b was synthesized starting from 17a following the general procedure H, as given in Example 9, as a white powder in 82% yield.

$^1$H NMR (400 MHz, DMSO) δ 10.08 (s, 1H), 7.56 (d, J=2.0 Hz, 1H), 7.37-7.25 (m, 3H), 7.16 (dd, J=8.6, 2.1 Hz, 1H), 7.00 (d, J=7.9 Hz, 2H), 6.95 (t, J=7.3 Hz, 1H), 4.38-4.28 (m, 4H), 2.05 (s, 3H).

$^{13}$C NMR (101 MHz, DMSO) δ 168.49, 158.27, 153.57, 139.44, 129.77, 129.51, 120.79, 114.57, 112.10, 104.83, 67.44, 66.03, 24.07. HRMS (ESI) calculated for $C_{16}H_{16}ClNO_3$ [M+Na]$^+$: 328.0711. Found: 328.0720.

4-chloro-3(2-phenoxy-ethoxy)-phenylamine (17c): The compound 17c was prepared starting from 17b following the general procedure I, as given in Example 10, in 80% yield.

$^1$H NMR (400 MHz, DMSO) δ 7.30 (t, J=7.5 Hz, 2H), 7.02-6.91 (m, 4H), 6.39 (d, J=1.1 Hz, 1H), 6.21-6.13 (m, 1H), 5.25 (s, 2H), 4.33-4.28 (m, 2H), 4.28-4.22 (m, 2H).

$^{13}$C NMR (101 MHz, DMSO) δ 158.29, 154.03, 149.10, 129.77, 129.47, 120.73, 114.56, 107.19, 99.82, 67.01, 66.14. HRMS (ESI) calculated for $C_{14}H_{14}ClNO_2$ [M+H]$^+$: 264.0786. Found: 264.0777.

6-chloro-3-ethyl-2-methyl-7-(2-phenoxy-ethoxy)-1H-quinolin-4-one (17): The compound 17 was prepared according to the general procedure A, as given in Example 2, in 60% yield as white crystalline compound, m.p.=290-292° C.

$^1$H NMR (400 MHz, DMSO) δ 11.38 (s, 1H), 7.97 (s, 1H), 7.31 (t, J=7.9 Hz, 2H), 7.06 (s, 1H), 7.02 (d, J=8.0 Hz, 2H), 6.96 (t, J=7.3 Hz, 1H), 4.49-4.37 (m, 4H), 2.47 (q, J=7.3 Hz, 2H), 2.36 (s, 3H), 0.98 (t, J=7.3 Hz, 3H).

$^{13}$C NMR (101 MHz, DMSO) δ 173.94, 158.23, 155.36, 145.43, 139.21, 129.50, 126.02, 120.84, 120.36, 118.09, 117.64, 114.58, 100.15, 67.77, 65.92, 17.87, 17.23, 13.38. HRMS (ESI) calculated for $C_{20}H_{20}ClNO_3$ [M+H]$^+$: 358.1204. Found: 358.1195.

Example 27

Synthesis of Compound (18)

N-[4-methyl-3-(2-phenoxy-ethoxy)-phenyl]-acetamide (18a): Acetic anhydride (1.25 mL, 12.2 mmol) was added to a solution of 5-amino-2-methyl phenol (1.0 g, 8.1 mmol) in acetic acid (6 mL), and the reaction was refluxed for 5 mins. Then the reaction mixture was cooled to room temperature and the product was solidified. It was filtered off and washed with water (4 mL) and dried to obtain the product along with the trace amount of O-acylated product. The mixture, to which was added 3-bromophenetole (1.33 g, 6.6 mmol) and Cs$_2$CO$_3$ (2.927 g, 9.0 mmol) in DMF (10 mL), was stirred overnight at 50° C. The reaction mixture was then diluted with water (10 mL) and extracted with ethyl acetate (3×20 mL). The combined extracts were dried over sodium sulfate and recrystallized from toluene to obtain the pure product 18a in 65% (yield over two steps) as an off-white solid.

$^1$H NMR (400 MHz, DMSO) δ 9.89 (s, 1H), 7.34 (s, 1H), 7.30 (t, J=7.9 Hz, 2H), 7.08-6.85 (m, 5H), 4.39-4.28 (m, 2H), 4.26-4.17 (m, 2H), 2.06 (s, 3H), 2.02 (s, 3H).

$^{13}$C NMR (101 MHz, DMSO) δ 168.08, 158.41, 156.24, 138.40, 130.20, 129.51, 120.73, 120.38, 114.57, 111.06, 103.21, 66.65, 66.21, 24.03, 15.43. HRMS (ESI) calculated for $C_{17}H_{19}NO_3$ [M+H]$^+$: 286.1438. Found: 286.1427.

4-methyl-3-(2-phenoxy-ethoxy)-phenylamine (18b): The compound 18b was prepared starting from 18a according to the general procedure I, as given in Example 10, in 77% yield.

$^1$H NMR (400 MHz, DMSO) δ 7.41-7.11 (m, 2H), 7.20-6.90 (m, 3H), 6.76 (d, J=8.3 Hz, 1H), 6.26 (d, J=2.0 Hz, 1H), 6.11 (dd, J=7.9, 2.0 Hz, 1H), 4.86 (s, 2H), 4.29 (dd, J=5.6, 3.5 Hz, 2H), 4.18 (dd, J=5.6, 3.5 Hz, 2H), 1.97 (s, 3H).

$^{13}$C NMR (101 MHz, DMSO) δ 158.45, 156.92, 147.88, 130.55, 129.49, 120.68, 114.56, 112.66, 106.22, 98.70, 66.34, 66.30, 15.17. HRMS (ESI) calculated for $C_{15}H_{17}NO_2$ [M+H]$^+$: 244.1332. Found: 244.1326.

3-ethyl-2,6-dimethyl-7-(2-phenoxy-ethoxy)-1H-quiolin-4-one (18): The compound 18 was prepared starting from 18b (633 mg, 2.6 mmol) according to the general procedure A, as given in Example 2, in 70% yield as a white powder, m.p.=280-282° C.

$^1$H NMR (250 MHz, DMSO) δ 11.16 (s, 1H), 7.79 (s, 1H), 7.31 (t, J=7.8 Hz, 2H), 6.98 (m, 3H), 6.86 (s, 1H), 4.38 (m, 4H), 2.47 (q, J=7.15 Hz, 2H), 2.34 (s, 3H), 2.18 (s, 3H), 0.97 (t, J=7.2 Hz, 3H).

$^{13}$C NMR (101 MHz, DMSO) δ 175.43, 159.59, 159.07, 145.03, 139.88, 130.19, 126.97, 122.92, 121.48, 120.52, 118.22, 115.29, 98.15, 67.53, 66.77, 18.57, 17.86, 16.62, 14.25. HRMS (ESI) calculated for $C_{21}H_{23}NO_3$ [M+H]$^+$: 338.1751. Found: 338.1748.

Example 28

Synthesis of Compound (19)

N-[4-methoxy-3-(2-phenoxy-ethoxy)-phenyl]-acetamide (19a): The compound 19a was prepared starting from 5-amino-2-methoxy phenol (800 mg, 5.75 mmol) according to the procedure described for the synthesis of 18a (as in Example 27) in 62% yield as white powder.

$^1$H NMR (400 MHz, DMSO) δ 9.80 (s, 1H), 7.35 (d, J=2.2 Hz, 1H), 7.30 (t, J=7.9 Hz, 2H), 7.10 (dd, J=8.7, 2.2 Hz, 1H), 6.99 (d, J=9.08 Hz, 1H), 6.95 (t, J=7.47 Hz, 2H), 6.89 (d, J=8.7 Hz, 1H), 4.30 (dd, J=5.5, 2.9 Hz, 2H), 4.23 (dd, J=5.5, 2.9 Hz, 2H), 3.71 (s, 3H), 2.01 (s, 3H).

$^{13}$C NMR (101 MHz, DMSO) δ 167.75, 158.26, 147.46, 144.88, 132.95, 129.49, 120.69, 114.47, 112.44, 111.57, 105.89, 67.11, 66.14, 55.72, 23.87. HRMS (ESI) calculated for $C_{17}H_{19}NO_4$ [M+H]$^+$: 302.1387. Found: 302.1377.

4-methoxy-3-(2-phenoxy-ethoxy)-phenylamine (19b): The compound 19b was prepared starting from 19a by following the general procedure I, as given in Example 10, in 89% yield as dark brown solid.

$^1$H NMR (400 MHz, Acetone) δ 7.33-7.25 (m, 2H), 7.02-6.97 (m, 2H), 6.97-6.91 (m, 1H), 6.88 (d, J=8.4 Hz, 1H), 6.39 (d, J=2.3 Hz, 1H), 6.26-6.18 (m, 1H), 4.39-4.30 (m, 4H), 3.77 (s, 3H).

$^{13}$C NMR (101 MHz, Acetone) δ 159.99, 149.92, 146.85, 130.38, 121.66, 115.55, 114.29, 112.49, 107.67, 103.52, 68.63, 67.61, 56.79. HRMS (ESI) calculated for $C_{15}H_{17}NO_3$ [M+H]$^+$: 260.1281. Found: 260.1271.

3-ethyl-6-methoxy-2-methyl-7-(2-phenoxy-methoxy)-1H-quinolin-4-one (19): The compound 19 was prepared starting from 19b following the general procedure A, as given in Example 2, in 79% yield as white powder, m.p.=228-229° C.

$^1$H NMR (400 MHz, DMSO) δ 11.15 (s, 1H), 7.40 (s, 1H), 7.27 (t, J=7.7 Hz, 2H), 7.05-6.77 (m, 4H), 4.36-4.28 (m, 4H), 3.77 (s, 3H), 2.45 (q, J=7.3 Hz, 2H), 2.31 (s, 3H), 0.94 (t, J=7.3 Hz, 3H).

$^{13}$C NMR (101 MHz, DMSO) δ 174.26, 158.21, 151.33, 145.95, 143.85, 134.56, 129.53, 120.79, 119.36, 117.56, 114.48, 104.73, 99.51, 67.10, 65.93, 55.35, 18.01, 17.17, 13.57. HRMS (ESI) calculated for $C_{21}H_{23}NO_4$ [M+H]$^+$: 354.1699. Found: 354.1700.

Example 29

Synthesis of Compound (20)

N-(4-chloro-3-methoxymethoxy phenyl)acetamide (20a): MOMCl (0.6 mL, 7.51 mmol) was added to a DCM (15 mL) solution of compound 17a (1.07 g, 5.78 mmol). N,N-diisopropylethylamine (1.8 mL, 10.4 mmol) was added at 0° C. to the reaction mixture. The mixture was warmed to room temperature and stirred overnight. Water (5 mL) was added and extracted with DCM (3×20 mL). The combined extracts were shaken with brine (10 mL) and dried over sodium sulfate. The product 20a was obtained (860 mg, 65% yield) after flash column chromatography as a white crystalline solid.

$^1$H NMR (400 MHz, Acetone) δ 9.25 (br s, 1H), 7.60 (d, J=2.2 Hz, 1H), 7.32 (dd, J=8.7, 2.2 Hz, 1H), 7.28 (d, J=8.7 Hz, 1H), 5.23 (s, 2H), 3.46 (s, 3H), 2.07 (s, 3H).

$^{13}$C NMR (101 MHz, Acetone) δ 169.12, 153.80, 140.44, 130.70, 114.17, 108.43, 95.92, 56.49, 24.36. HRMS (ESI) calculated for $C_{10}H_{12}ClNO_3$ [M+Na]$^+$: 252.0398. Found: 252.0389.

4-chloro-3-methoxymethoxy-phenylamine (20b): The compound 20b was prepared according to the general procedure I, as given in Example 10, starting from 20a (700 mg, 3.05 mmol) in 84% yield as dark brown solid.

$^1$H NMR (400 MHz, DMSO) δ 6.99 (d, J=8.5 Hz, 1H), 6.44 (d, J=2.5 Hz, 1H), 6.20 (dd, J=8.5, 2.5 Hz, 1H), 5.27 (s, 2H), 5.15 (s, 2H), 3.39 (s, 3H).

$^{13}$C NMR (101 MHz, DMSO) δ 152.64, 149.00, 129.73, 108.32, 108.03, 101.96, 94.34, 55.70. HRMS (ESI) calculated for $C_8H_{10}ClNO_2$ [M+H]$^+$: 188.0473. Found: 188.0476.

6-chloro-3-ethyl-7-methoxymethoxy-2-methyl-1H-quinoline-4-one (20): The compound 20 was synthesized by following the general procedure A, as given in Example 2, starting from the aniline 20b in 17% yield as light brown powder, m.p.=217-219° C.

$^1$H NMR (400 MHz, DMSO) δ 11.39 (s, 1H), 7.99 (s, 1H), 7.22 (s, 1H), 5.37 (s, 2H), 3.45 (d, J=1.2 Hz, 3H), 2.46 (q, J=7.2 Hz, 2H), 2.34 (s, 3H), 0.98 (t, J=7.1 Hz, 3H).

$^{13}$C NMR (101 MHz, DMSO) δ 173.91, 153.88, 145.66, 138.97, 125.98, 120.31, 118.67, 118.11, 102.52, 94.83, 56.02, 17.87, 17.19, 13.36. HRMS (ESI) calculated for $C_{14}H_{16}ClNO_3$ [M+H]$^+$: 282.0892. Found: 282.0889.

Example 30

Synthesis of compounds (21) and (22)

N-[4-chloro-3-(3-hydroxy-propoxy)-phenyl]-acetamide (21a): The compound 21a was prepared starting from 17a by following the general procedure H, as given in Example 9, in 60% yield as an off-white solid.

$^1$H NMR (400 MHz, DMSO) δ 10.04 (s, 1H), 7.49 (d, J=2.0 Hz, 1H), 7.30 (d, J=8.6 Hz, 1H), 7.12 (dd, J=8.6, 2.1 Hz, 1H), 4.58 (t, J=5.1 Hz, 1H), 4.05 (t, J=6.3 Hz, 2H), 3.58 (dd, J=11.3, 5.9 Hz, 2H), 2.03 (s, 3H), 1.94-1.81 (m, 2H).

$^{13}$C NMR (101 MHz, DMSO) δ 168.43, 153.78, 139.41, 129.56, 114.83, 111.57, 104.47, 65.47, 57.11, 31.91, 24.04. HRMS (ESI) calculated for $C_{11}H_{14}ClNO_3$ [M+H]$^+$: 244.0735. Found: 244.0734.

3-(5-amino-2-chloro-phenoxy)-propan-1-ol (21b): The compound 21b was prepared starting from 21a following the general procedure I in 67% yield as a light brown solid.

$^1$H NMR (400 MHz, DMSO) δ 6.95 (d, J=8.4 Hz, 1H), 6.32 (d, J=2.4 Hz, 1H), 6.12 (dd, J=8.5, 2.4 Hz, 1H), 5.20 (s, 2H), 4.53 (t, J=5.1 Hz, 1H), 3.97 (t, J=6.3 Hz, 2H), 3.60-3.53 (m, 2H), 1.85 (t, J=6.3 Hz, 2H).

$^{13}$C NMR (101 MHz, DMSO) δ 154.25, 149.06, 129.56, 106.68, 99.54, 95.81, 65.02, 57.21, 32.04. HRMS (ESI) calculated for $C_9H_{12}ClNO_2$ [M+Na]$^+$: 224.0449. Found: 224.0455.

Compounds (21) and (22): The above mixture of the compounds was prepared starting from 21b following the general procedure A, as given in Example 2, in 21% yield (over the mixture of the regular product 21 and a transesterification product 22). The mixture was separated by preparative HPLC by dissolving in minimal amount of methanol.

6-chloro-3-ethyl-7-(3-hydroxy-propoxy)-2-methyl-1H-quinolin-4-one (21): $^1$H NMR (400 MHz, DMSO) δ 11.31 (br s, 1H), 7.94 (s, 1H), 6.98 (s, 1H), 4.60 (br s, 1H), 4.15 (t, J=6.2 Hz, 2H), 3.59 (d, J=5.0 Hz, 2H), 2.45 (q, J=7.4 Hz, 2H), 2.33 (s, 3H), 1.97-1.88 (m, 2H), 0.96 (t, J=7.4 Hz, 3H).

$^{13}$C NMR (101 MHz, DMSO) δ 173.97, 155.60, 145.34, 139.31, 125.85, 120.27, 117.82, 117.73, 99.75, 65.82, 57.01, 31.68, 17.87, 17.25, 13.40. HRMS (ESI) calculated for $C_{15}H_{18}ClNO_3$ [M+H]$^+$: 296.1048. Found: 296.1046.

2-ethyl-3-oxo-butyricacid-3-(6-chloro-3-ethyl-2-methyl-4-oxo-1,4-dihydro-quinolin-7-yloxy)-propyl ester (22): $^1$H NMR (400 MHz, CDCl$_3$) δ 9.46 (s, 1H), 8.31 (s, 1H), 6.68 (s, 1H), 4.36 (dt, J=11.1, 5.5 Hz, 1H), 4.25 (dt, J=11.3, 5.6 Hz, 1H), 4.15 (t, J=6.6 Hz, 2H), 3.45 (t, J=7.4 Hz, 1H), 2.62 (q, J=7.83 Hz, 2H), 2.43 (s, 3H), 2.27 (s, 3H), 2.21-2.09 (m, 2H), 2.01-1.83 (m, 2H), 1.09 (t, J=7.3 Hz, 3H), 0.95 (t, J=7.4 Hz, 3H).

$^{13}$C NMR (101 MHz, CDCl$_3$) δ 175.90, 168.89, 156.24, 144.63, 139.00, 127.74, 122.08, 119.77, 118.87, 98.85, 65.33, 61.67, 61.52, 29.41, 27.98, 21.82, 18.68, 18.25, 13.45, 11.97. HRMS (ESI) calculated for $C_{21}H_{26}ClNO_5$ [M+Na]$^+$: 430.1392. Found: 430.1391.

Example 31

Synthesis of Compound (23)

N-[4-chloro-3-(2-morpholin-4-yl-ethoxy)-phenyl]-acetamide (23a): The compound 23a was prepared by using the general procedure H, as given in Example 9, in 69% yield starting from 17a, with 2.5 eq of cesium carbonate and 1.1 eq of 4-(2-chloroethyl) morpholine hydrochloride.

$^1$H NMR (400 MHz, DMSO) δ 9.97 (s, 1H), 7.43 (s, 1H), 7.22 (dd, J=8.6, 1.5 Hz, 1H), 7.05 (d, J=8.6 Hz, 1H), 4.02 (t, J=5.4 Hz, 2H), 3.59-3.41 (m, 4H), 2.65 (t, J=5.3 Hz, 2H), 2.48-2.38 (m, 4H), 1.96 (s, 3H).

$^{13}$C NMR (101 MHz, DMSO) δ 168.48, 153.63, 139.44, 129.65, 114.89, 111.81, 104.61, 66.81, 66.23, 56.61, 53.74, 24.08. HRMS (ESI) calculated for $C_{14}H_{19}ClN_2O_3$ [M+Na]$^+$: 321.0976. Found: 321.0971.

4-chloro-3-(2-morpholin-4-yl-ethoxy)-phenylamine (23b): The compound 23b was prepared starting from 23a according to the general procedure I, as given in Example 10, in 87% yield.

$^1$H NMR (400 MHz, DMSO) δ 6.93 (d, J=8.5 Hz, 1H), 6.30 (d, J=2.2 Hz, 1H), 6.10 (dd, J=8.5, 2.2 Hz, 1H), 5.17 (s, 2H), 3.99 (t, J=5.8 Hz, 2H), 3.56-3.51 (m, 4H), 2.66 (t, J=5.8 Hz, 2H), 2.47 (d, J=3.9 Hz, 4H).

$^{13}$C NMR (101 MHz, DMSO) δ 154.09, 149.05, 129.63, 107.24, 106.91, 99.65, 66.45, 66.19, 56.73, 53.71. HRMS (ESI) calculated for $C_{12}H_{17}ClN_2O_2$ [M+H]$^+$: 257.10513. Found: 257.10397.

6-chloro-3-ethyl-2-methyl-7-(2-morpholin-4-yl-ethoxy)-1H-quinolin-4-one (23): The compound 23 was synthesized starting from aniline 23b by following the general procedure A, as given in Example 2, in 12% yield as beige powder, m.p.=270-271° C.

$^1$H NMR (400 MHz, DMSO) δ 11.29 (s, 1H), 7.93 (s, 1H), 6.95 (s, 1H), 4.18 (t, J=5.4 Hz, 2H), 3.65-3.47 (m, 4H), 2.76 (t, J=5.2 Hz, 2H), 2.60-2.37 (m, 6H), 2.32 (s, 3H), 0.94 (t, J=7.3 Hz, 3H).

$^{13}$C NMR (101 MHz, DMSO) δ 174.65, 156.10, 146.08, 139.93, 126.60, 121.01, 118.63, 118.37, 100.60, 67.96, 66.88, 57.04, 54.40, 18.55, 17.92, 14.08. HRMS (ESI) calculated for $C_{18}H_{23}ClN_2O_3$ [M+H]$^+$: 351.1470. Found: 351.1463.

Example 32

Synthesis of Compound (24)

N-[4-chloro-3-(2-dimethylamino-ethoxy)-phenyl]-acetamide (24a): The compound 24a was prepared starting from 17a and 2-dimethylamino ethyl chloride hydrochloride, following the general procedure H, as given in Example 9, in 80% yield.

$^1$H NMR (400 MHz, DMSO) δ 10.04 (s, 1H), 7.49 (d, J=2.1 Hz, 1H), 7.30 (d, J=8.6 Hz, 1H), 7.13 (dd, J=8.6, 2.2 Hz, 1H), 4.06 (t, J=5.8 Hz, 2H), 2.68 (t, J=5.7 Hz, 2H), 2.25 (s, 6H), 2.04 (s, 3H). HRMS (ESI) calculated for $C_{12}H_{17}ClN_2O_2$ [M+H]$^+$: 257.1051. Found: 257.1042.

4-chloro-3-(2-dimethylamino-ethoxy)-phenylamine (24b): The compound 24b was prepared starting from 24a according to the general procedure I, as given in Example 10, in 81% yield.

¹H NMR (400 MHz, DMSO) δ 6.96 (d, J=8.5 Hz, 1H), 6.33 (d, J=2.4 Hz, 1H), 6.13 (dd, J=8.5, 2.4 Hz, 1H), 5.21 (s, 2H), 4.00 (t, J=5.8 Hz, 2H), 2.67 (t, J=5.8 Hz, 2H), 2.26 (s, 6H).

¹³C NMR (101 MHz, DMSO) δ 154.09, 149.07, 129.65, 107.19, 106.87, 99.55, 66.54, 57.35, 45.57. HRMS (ESI) calculated for $C_{10}H_{15}ClN_2O$ [M+H]⁺: 215.0946. Found: 215.0937.

6-chloro-7-(2-dimethylamino-ethoxy)-3-ethyl-2-methyl-1H-quinolin-4-one (24): The compound 24 was prepared starting from 24b according to the general procedure A, as given in Example 2, in 53% yield as a light brown solid, m.p.=227-230° C.

¹H NMR (250 MHz, DMSO) δ 11.34 (s, 1H), 7.92 (s, 1H), 6.96 (s, 1H), 4.15 (t, J=5.7 Hz, 2H), 2.71 (t, J=5.7 Hz, 2H), 2.43 (q, J=7.54 Hz, 2H), 2.32 (s, 3H), 2.24 (s, 6H), 0.94 (t, J=7.54 Hz, 3H).

¹³C NMR (101 MHz, DMSO) δ 173.93, 155.39, 145.41, 139.28, 125.87, 120.26, 117.90, 117.65, 99.82, 67.45, 57.05, 45.66, 17.87, 17.18, 13.39. HRMS (ESI) calculated for $C_{16}H_{21}ClN_2O_2$ [M+H]⁺: 309.1364. Found: 309.1364.

Example 33

Synthesis of Compound (25)

2-bromo-5-nitro-phenol (25a): BBr₃ (8.58 mL of 1.0M solution, 8.6 mmol) was added to the DCM (10 mL) solution of 1-bromo-2-methoxy-4-nitrobenzene (1.0 g, 4.3 mmol) at 0° C. The reaction mixture was warmed to room temperature and stirred overnight. The mixture was quenched with water and extracted with ethyl acetate (3×20 mL). The combined extracts were dried and the crude was purified by flash column chromatography to get the desired compound as pale brown powder in 65% yield (600 mg).

¹H NMR (400 MHz, CDCl₃) δ 7.84 (s, 1H), 7.79-7.59 (m, 2H), 5.92 (br s, 1H).

¹³C NMR (101 MHz, CDCl₃) δ 152.97, 148.49, 132.62, 117.44, 116.43, 111.20.

1-bromo-4-nitro-2-(2-phenoxy-ethoxy)-benzene (25b): The compound 25b was prepared by using the general procedure H, as given in Example 9, starting from compound 25a as pale yellow solid in 80% yield.

¹H NMR (400 MHz, CDCl₃) δ 7.86 (d, J=2.3 Hz, 1H), 7.77-7.66 (m, 2H), 7.33-7.26 (m, 2H), 7.00-6.93 (m, 3H), 4.49 (dd, J=5.6, 3.5 Hz, 2H), 4.41 (dd, J=6.0, 3.5 Hz, 2H).

¹³C NMR (101 MHz, CDCl₃) δ 158.37, 133.68, 129.55, 121.38, 120.28, 116.91, 114.73, 108.08, 68.58, 66.18. HRMS (ESI) calculated for $C_{14}H_{12}BrNO_4$ [M+H]⁺: 359.9842. Found: 359.9855.

4-bromo-3-(2-phenoxy-ethoxy)-phenylamine (25c): Acetic acid (1.068 mL, 18 mmol) was added to the mixture of 25b (600 mg, 1.8 mmol) and zinc dust (1.157 g, 18.0 mmol) in ethanol (10 mL) at 0° C. The reaction mixture was warmed to room temperature and stirred for 4 hrs. The mixture was filtered, the solvent distilled off under reduced pressure and the crude was purified by flash column chromatography to obtain the aniline 25c in 84% yield.

¹H NMR (400 MHz, DMSO) δ 7.33-7.26 (m, 2H), 7.11 (d, J=8.5 Hz, 1H), 7.02-6.98 (m, 2H), 6.97-6.92 (m, 1H), 6.37 (d, J=2.4 Hz, 1H), 6.13 (dd, J=8.5, 2.4 Hz, 1H), 5.28 (s, 2H), 4.31 (dd, J=5.3, 3.0 Hz, 2H), 4.24 (dd, J=5.8, 2.8 Hz, 2H).

¹³C NMR (101 MHz, DMSO) δ 158.77, 155.38, 150.21, 133.10, 129.94, 121.20, 115.06, 108.45, 100.28, 67.56, 66.64. HRMS (ESI) calculated for $C_{14}H_{14}BrNO_2$ [M+H]⁺: 308.0281. Found: 308.0268.

6-bromo-3-ethyl-2-methyl-7-(2-phenoxy-ethoxy)-1H-quinolin-4-one (25): The compound 25 was prepared starting from 25c according to the general procedure A, as given in Example 2, in 15% yield as the mixture of two isomers. The required isomer 25 was separated by preparative HPLC by dissolving the mixture in minimal amount of methanol.

¹H NMR (400 MHz, DMSO) δ 11.32 (s, 1H), 8.11 (s, 1H), 7.27 (t, J=7.8 Hz, 2H), 7.11-6.78 (m, 4H), 4.39 (m, 4H), 2.43 (q, J=7.3 Hz, 2H), 2.32 (s, 3H), 0.94 (t, J=7.3 Hz, 3H).

¹³C NMR (101 MHz, DMSO) δ 173.93, 158.36, 156.01, 145.72, 139.90, 129.48, 120.88, 120.49, 118.80, 114.55, 106.78, 99.92, 67.90, 66.08, 17.88, 17.24, 13.40. HRMS (ESI) calculated for $C_{20}H_{20}BrNO_3$ [M+H]⁺: 424.0519. Found: 424.0517.

Example 34

Synthesis of Compound (26)

2-(3-bromo-propoxy)-1-chloro-4-nitro benzene (26a): 1,3-dibromo propane (1.3 mL, 12.65 mmol) and cesium carbonate (4.1 g, 12.65 mmol) was added to the DMF (18 mL) solution of 2-chloro-5-nitro phenol (2.0 g, 11.5 mmol) and the reaction mixture stirred overnight at room temperature. Water (20 mL) was added to the mixture, extracted with DCM (3×25 mL) and combined extracts were dried over sodium sulfate and concentrated in vacuo. The crude product was purified by flash column chromatography to get the title compound 26a in 64% (2.176 g) yield as colorless oil.

¹H NMR (400 MHz, CDCl₃) δ 7.82-7.74 (m, 2H), 7.49 (d, J=9.0 Hz, 1H), 4.26 (t, J=5.7 Hz, 2H), 3.64 (t, J=6.3 Hz, 2H), 2.45-2.34 (m, 2H).

¹³C NMR (101 MHz, CDCl₃) δ 154.50, 147.22, 130.41, 130.31, 116.46, 107.79, 66.95, 31.82, 29.37.

1-[3-(2-chloro-5-nitro-phenoxy)-propyl]-4-phenyl-piperazine (26b): To the compound 26a (2.1 g, 7.1 mmol) in DMF (9 mL) was added N-phenyl piperazine (1.16 g, 7.1 mmol) and potassium carbonate (1.28 g, 9.23 mmol). The mixture was stirred for 18 hrs. at room temperature. Water (10 mL) was added to the reaction mixture and extracted with ethyl acetate (3×20 mL). The combined extracts were dried over sodium sulfate and concentrated under reduced pressure. The crude product was purified by flash column chromatography to get the title compound 26b in 78% yield as yellow solid.

¹H NMR (400 MHz, CDCl₃) δ 7.80-7.73 (m, 2H), 7.49 (dd, J=8.1, 0.8 Hz, 1H), 7.29-7.21 (m, 2H), 6.95-6.89 (m, 2H), 6.88-6.80 (m, 1H), 4.21 (t, J=6.3 Hz, 2H), 3.27-3.13 (m, 4H), 2.70-2.53 (m, 6H), 2.17-2.05 (m, 2H).

¹³C NMR (101 MHz, CDCl₃) δ 154.84, 151.22, 147.18, 130.28, 130.20, 129.03, 119.61, 116.06, 115.97, 107.68, 67.86, 54.64, 53.24, 49.08, 26.26. HRMS (ESI) calculated for $C_{19}H_{22}ClN_3O_3$ [M+H]⁺: 376.1423. Found: 376.1411.

4-chloro-3-[3-(4-phenyl-piperzin-1-yl)-propoxy]-phenylamine (26c): The compound 26c was prepared starting from 26b following the procedure described for the synthesis of 25c in 76% yield as a white solid.

¹H NMR (400 MHz, DMSO) δ 7.15 (t, J=7.9 Hz, 2H), 6.92 (d, J=8.5 Hz, 1H), 6.86 (d, J=8.1 Hz, 2H), 6.71 (t, J=7.2 Hz, 1H), 6.28 (d, J=1.9 Hz, 1H), 6.08 (dd, J=8.5, 2.0 Hz, 1H), 5.16 (s, 2H), 3.92 (t, J=6.3 Hz, 2H), 3.11-3.03 (m, 4H), 2.51-2.40 (m, 6H), 1.95-1.76 (m, 2H).

¹³C NMR (101 MHz, DMSO) δ 154.24, 150.99, 149.07, 129.60, 128.84, 118.67, 115.26, 107.32, 106.78, 99.65, 66.32, 54.30, 52.76, 48.16, 26.11. HRMS (ESI) calculated for $C_{19}H_{24}ClN_3O$ [M+H]⁺: 346.1681. Found: 346.1669.

6-chloro-3-ethyl-2-methyl-7-[3-(4-phenyl-piperazin-1-yl)-propoxy]-1H-quinolin-4-one (26): The compound 26 was prepared staring from aniline 26c (306 mg, 0.886 mmol)

following the general procedure A, as given in Example 2, to get the title compound 26 in 22% yield as white crystalline, m.p.=253-255° C.

$^1$H NMR (400 MHz, DMSO) δ 11.29 (s, 1H), 7.94 (s, 1H), 7.18 (t, J=7.9 Hz, 2H), 6.98 (s, 1H), 6.90 (d, J=8.3 Hz, 2H), 6.75 (d, J=7.2 Hz, 1H), 4.14 (t, J=6.2 Hz, 2H), 3.15-3.05 (m, 4H), 2.63-2.36 (m, 8H), 2.32 (s, 3H), 2.06-1.94 (m, 2H), 0.95 (t, J=7.3 Hz, 3H).

$^{13}$C NMR (101 MHz, DMSO) δ 173.98, 155.57, 150.99, 145.34, 139.29, 128.87, 125.88, 120.29, 118.73, 117.86, 117.73, 115.30, 99.84, 67.22, 54.20, 52.75, 48.19, 25.78, 19.77, 17.87, 17.26, 13.41. HRMS (ESI) calculated for $C_{25}H_{30}ClN_3O_2$ [M+H]$^+$: 440.2099. Found: 440.2098.

Example 35

3-ethyl-2-methyl-7-(2-phenoxyethoxy)quinolin-4(1H)-one (27): $^1$H NMR (400 MHz, CDCl$_3$) δ 11.20 (s, 1H), 8.03-7.88 (m, 1H), 7.31 (t, J=7.8 Hz, 2H), 6.97 (dd, J=20.1, 7.7 Hz, 3H), 6.89 (d, J=6.9 Hz, 2H), 4.36 (s, 4H), 2.47 (d, J=7.5 Hz, 2H), 2.35 (s, 3H), 0.98 (t, J=7.3 Hz, 3H).

$^{13}$C NMR (101 MHz, DMSO) δ 175.01, 160.32, 158.23, 144.95, 140.72, 129.53, 127.01, 120.79, 120.00, 118.06, 114.60, 114.48, 112.45, 99.07, 66.57, 66.01, 17.87, 17.21, 13.53.

Example 36

6-butyl-3-iodo-2-methyl-7-(2-phenoxyethoxy)quinolin-4(1H)-one (28): Following general procedure B, as given in Example 3, the title compound was prepared from 15 in 89% yield as a light yellow powder.

$^1$H NMR (400 MHz, DMSO) δ 7.78 (s, 1H), 7.31 (t, J=7.7 Hz, 2H), 7.02-6.92 (m, 4H), 4.40 (s, 4H), 2.61 (d, J=10.1 Hz, 5H), 1.57-1.49 (m, 2H), 1.26 (dt, J=14.6, 7.3 Hz, 2H), 0.83 (t, J=7.3 Hz, 3H).

Example 37

6-butyl-4-ethoxy-3-iodo-2-methyl-7-(2-phenoxyethoxy) quinolone (30): Following general procedure C, as given in Example 4, the title compound was prepared in 77% yield as a beige solid.

$^1$H NMR (400 MHz, CDCl$_3$) δ 7.68 (s, 1H), 7.35-7.24 (m, 3H), 6.95 (t, J=7.1 Hz, 3H), 4.40 (dd, J=17.5, 5.0 Hz, 4H), 4.16 (q, J=7.0 Hz, 2H), 2.89 (s, 3H), 2.77-2.71 (m, 2H), 1.62 (dt, J=14.0, 7.3 Hz, 5H), 1.34 (dt, J=14.5, 7.4 Hz, 2H), 0.90 (t, J=7.3 Hz, 3H).

$^{13}$C NMR (101 MHz, CDCl$_3$) δ 162.58, 160.66, 158.99, 158.66, 149.45, 133.56, 129.48, 121.57, 121.09, 117.57, 114.71, 106.65, 87.05, 70.66, 66.76, 66.22, 31.64, 30.44, 30.38, 22.46, 15.81, 13.95.

Example 38

6-butyl-2-methyl-7-(2-phenoxyethoxy)-3-phenylquinolin-4(1H)-one (31): Following general procedure E, as given in Example 6, the title compound was prepared in 49% yield.

$^1$H NMR (400 MHz, DMSO) δ 11.44 (s, 1H), 7.80 (s, 1H), 7.37 (t, J=7.2 Hz, 2H), 7.33-7.25 (m, 3H), 7.22 (d, J=7.6 Hz, 2H), 7.02-6.93 (m, 4H), 4.40 (d, J=4.9 Hz, 4H), 2.60 (t, J=7.4 Hz, 2H), 2.17 (s, 3H), 1.57-1.49 (m, 2H), 1.25 (dd, J=14.6, 7.3 Hz, 2H), 0.83 (dd, J=7.8, 6.7 Hz, 3H).

$^{13}$C NMR (101 MHz, DMSO) δ 174.34, 159.14, 158.42, 145.43, 139.42, 136.46, 131.02, 129.51, 127.66, 127.36, 126.27, 125.86, 120.78, 120.46, 118.35, 114.54, 97.88, 66.84, 66.09, 31.41, 29.26, 21.81, 18.76, 13.74. HRMS (ESI) calculated for $C_{28}H_{29}NO_3$ [M+H]$^+$: 428.2220. found 428.2225.

Example 39

6-butyl-2-methyl-7-(2-phenoxyethoxy)-3-(pyridin-4-yl) quinolin-4(1H)-one (32): Following general procedure E, as given in Example 6, the title compound was prepared in 41% yield.

$^1$H NMR (400 MHz, DMSO) δ 11.62 (s, 1H), 8.56 (d, J=4.2 Hz, 2H), 7.80 (s, 1H), 7.30 (dd, J=13.1, 5.8 Hz, 4H), 7.04-6.90 (m, 4H), 4.40 (s, 4H), 2.60 (t, J=7.5 Hz, 2H), 1.57-1.48 (m, 2H), 1.24 (dt, J=14.4, 7.4 Hz, 2H), 0.83 (t, J=7.3 Hz, 3H).

$^{13}$C NMR (101 MHz, DMSO) δ 173.70, 159.38, 158.42, 148.96, 145.97, 144.53, 139.43, 129.52, 127.81, 126.35, 125.79, 120.80, 118.25, 117.87, 114.55, 98.04, 66.91, 66.09, 31.35, 29.25, 21.81, 18.71, 13.74. HRMS (ESI) calculated for $C_{27}H_{28}N_2O_3$ [M+H]$^+$: 429.2173. found 429.2179.

Example 40

6-butyl-2-methyl-7-(2-phenoxyethoxy)-3-(pyridin-3-yl) quinolin-4(1H)-one (33): Following general procedure E, as given in Example 6, the title compound was prepared in 36% yield.

$^1$H NMR (400 MHz, DMSO) δ 11.59 (s, 1H), 8.46 (d, J=11.9 Hz, 2H), 7.81 (s, 1H), 7.67 (d, J=7.6 Hz, 1H), 7.45-7.37 (m, 1H), 7.31 (t, J=7.6 Hz, 2H), 6.98 (dd, J=21.4, 9.4 Hz, 4H), 4.41 (s, 4H), 2.61 (t, J=7.5 Hz, 2H), 1.53 (dt, J=15.1, 7.6 Hz, 2H), 1.25 (dd, J=14.6, 7.4 Hz, 2H), 0.83 (t, J=7.3 Hz, 3H).

$^{13}$C NMR (101 MHz, DMSO) δ 174.69, 159.76, 158.85, 151.91, 147.70, 146.62, 139.93, 138.94, 132.54, 129.95, 128.14, 126.23, 123.35, 121.22, 118.61, 117.33, 114.98, 98.44, 67.32, 66.52, 31.80, 29.69, 22.25, 19.20, 14.18. HRMS (ESI) calculated for $C_{27}H_{28}N_2O_3$ [M+H]$^+$: 429.2173. found 429.2172.

Example 41

6-butyl-2-methyl-7-(2-phenoxyethoxy)-3-(4-(trifluoromethyl)phenyl)quinolin-4(1H)-one (34): Following procedure D, as given in Example 5, the title compound was prepared in 60% yield.

$^1$H NMR (400 MHz, DMSO) δ 11.56 (s, 1H), 7.80 (s, 1H), 7.72 (d, J=8.1 Hz, 2H), 7.48 (d, J=8.0 Hz, 2H), 7.31 (t, J=7.9 Hz, 2H), 7.03-6.94 (m, 4H), 4.41 (s, 4H), 2.61 (t, J=7.4 Hz, 2H), 2.21 (s, 3H), 1.58-1.49 (m, 2H), 1.24 (dt, J=14.6, 7.3 Hz, 2H), 0.83 (t, J=7.3 Hz, 3H).

$^{19}$F NMR (376 MHz, DMSO) δ −61.19.

$^{13}$C NMR (101 MHz, DMSO) δ 174.69, 160.01, 159.10, 146.52, 141.69, 140.13, 132.60, 130.20, 128.37, 127.55 (q, J=31.31 Hz), 126.50, 125.13, 123.84, 121.47, 119.72, 118.95, 115.22, 98.67, 67.56, 66.76, 32.06, 29.94, 22.49, 19.42, 14.42. HRMS (ESI) calculated for $C_{29}H_{28}F_3NO_3$ [M+H]$^+$: 496.2094. found 496.2097.

Example 42

6-butyl-2-methyl-7-(2-phenoxyethoxy)-3-(4-(trifluoromethoxy)phenyl)quinolin-4(1H)-one (35): Following general procedure E, as given in Example 6, the title compound was prepared in 37% yield.

$^1$H NMR (400 MHz, DMSO) δ 11.53 (s, 1H), 7.80 (s, 1H), 7.37-7.29 (m, 6H), 7.02-6.94 (m, 4H), 4.40 (d, J=2.7 Hz, 4H), 2.63-2.57 (m, 2H), 2.19 (s, 3H), 1.54 (dd, J=14.9, 7.3 Hz, 2H), 1.25 (dd, J=14.8, 7.4 Hz, 2H), 0.83 (t, J=7.3 Hz, 3H)

$^{19}$F NMR (376 MHz, DMSO) δ −56.62.

$^{13}$C NMR (101 MHz, DMSO) δ 174.18, 159.28, 158.43, 146.84, 145.77, 139.45, 135.79, 132.93, 129.53, 127.59, 125.82, 121.46, 120.80, 120.27, 119.00, 118.92, 118.25, 114.54, 97.94, 66.88, 66.09, 31.41, 29.29, 21.83, 18.79, 13.76. HRMS (ESI) calculated for $C_{29}H_{28}F_3NO_4$ [M+H]$^+$: 512.2043. found 512.2046.

Example 43

6-butyl-3-(3-(4-fluorophenoxy)phenyl)-2-methyl-7-(2-phenoxyethoxy)quinolin-4(1H)-one (36): Following general procedure E, as given in Example 6, the title compound was prepared in 71% yield.

$^1$H NMR (400 MHz, DMSO) δ 11.48 (s, 1H), 7.79 (s, 1H), 7.38 (t, J=7.9 Hz, 1H), 7.30 (dd, J=11.9, 4.1 Hz, 2H), 7.22 (t, J=8.8 Hz, 2H), 7.11-7.06 (m, 2H), 7.01-6.86 (m, 7H), 4.39 (d, J=5.4 Hz, 4H), 2.59 (t, J=7.5 Hz, 2H), 2.20 (s, 3H), 1.52 (dt, J=14.8, 7.4 Hz, 2H), 1.24 (dd, J=14.7, 7.4 Hz, 2H), 0.83 (t, J=7.3 Hz, 3H).

$^{19}$F NMR (376 MHz, DMSO) δ −120.09.

$^{13}$C NMR (101 MHz, DMSO) δ 174.10, 159.18, 158.05 (d, J=240.4 Hz), 158.40, 156.46, 152.72 (d, J=2.02 Hz), 145.59, 139.37, 138.40, 129.48, 129.15, 127.46, 126.20, 125.80, 120.89, 120.76, 120.41 (d, J=7.07 Hz), 119.66, 118.29, 116.81 (d, J=23.23 Hz), 116.15, 114.53, 97.89, 66.84, 66.08, 31.36, 29.21, 21.78, 18.76, 13.70. HRMS (ESI) calculated for $C_{34}H_{32}FNO_4$ [M+H]$^+$: 538.2388. found 538.2386.

Example 44

6-butyl-2-methyl-7-(2-phenoxyethoxy)-3-(4-((4-(trifluoromethoxy)phenoxy)methyl)phenyl) quinolin-4(1H)-one (37): Following general procedure E, as given in Example 6, the title compound was prepared in 69% yield.

$^1$H NMR (400 MHz, DMSO) δ 11.41 (s, 1H), 7.76 (s, 1H), 7.42 (d, J=8.0 Hz, 2H), 7.30-7.25 (m, 4H), 7.22 (d, J=7.9 Hz, 2H), 7.11 (d, J=9.0 Hz, 2H), 7.01-6.87 (m, 5H), 5.11 (s, 2H), 4.37 (d, J=3.4 Hz, 4H), 2.59-2.54 (m, 2H), 2.16 (s, 3H), 1.54-1.47 (m, 2H), 1.24-1.17 (m, 2H), 0.80 (t, J=7.3 Hz, 3H).

$^{19}$F NMR (376 MHz, DMSO) δ −57.31.

$^{13}$C NMR (101 MHz, DMSO) δ 174.61, 159.63, 158.84, 157.76, 146.22, 146.00, 142.25, 139.84, 136.60, 134.97, 131.56, 129.96, 127.90, 127.74, 126.29, 122.95, 121.23, 120.50, 118.73, 116.37, 114.97, 98.33, 70.19, 67.30, 66.53, 31.83, 29.70, 22.24, 19.22, 14.17. HRMS (ESI) calculated for $C_{36}H_{34}F_3NO_5$ [M+H]$^+$: 618.2462. found 618.2461.

Example 45

6-butyl-2-methyl-3-(2-methyl-4-(4-(trifluoromethoxy)phenoxy)phenyl)-7-(2-phenoxyethoxy)-quinolin-4(1H)-one (38): Following general procedure F, as given in Example 7, the title compound was prepared in 49% yield. This reaction was performed in a microwave reactor at a temperature of 110° C.

$^1$H NMR (400 MHz, DMSO) δ 11.44 (s, 1H), 7.75 (s, 1H), 7.37 (d, J=8.7 Hz, 2H), 7.28 (t, J=7.6 Hz, 2H), 7.11 (d, J=9.0 Hz, 2H), 7.02-6.91 (m, 6H), 6.83 (d, J=8.1 Hz, 1H), 4.37 (s, 4H), 2.59-2.54 (m, 2H), 2.03 (s, 3H), 1.98 (s, 3H), 1.54-1.47 (m, 2H), 1.22 (dd, J=14.7, 7.5 Hz, 2H), 0.80 (t, J=7.2 Hz, 3H).

$^{19}$F NMR (376 MHz, DMSO) δ −57.31.

$^{13}$C NMR (101 MHz, DMSO) δ 170.34, 159.91, 158.35, 155.68, 155.55, 149.41, 143.58, 139.93, 139.59, 132.55, 130.11, 130.04, 129.47, 124.82, 122.80, 121.35, 120.78, 120.09, 119.70, 118.79, 118.52, 116.20, 114.45, 98.20, 67.16, 65.98, 31.24, 29.42, 21.84, 19.36, 18.67, 13.67. HRMS (ESI) calculated for $C_{36}H_{34}F_3NO_5$ [M+H]$^+$: 618.2462. found 618.2450.

Example 46

6-butyl-2-methyl-3-(2-methyl-4-(trifluoromethyl)phenyl)-7-(2-phenoxyethoxy)quinolin-4(1H)-one (39): Following general procedure E, as given in Example 6, the title compound was prepared in 13% yield.

$^1$H NMR (400 MHz, DMSO) δ 11.57 (s, 1H), 7.79 (s, 1H), 7.63 (s, 1H), 7.53 (d, J=8.0 Hz, 1H), 7.33-7.25 (m, 3H), 7.03-6.94 (m, 4H), 4.41 (s, 4H), 2.60 (t, J=7.4 Hz, 2H), 2.12 (s, 3H), 2.04 (s, 3H), 1.57-1.49 (m, 2H), 1.26 (dd, J=14.6, 7.3 Hz, 2H), 0.83 (t, J=7.2 Hz, 3H).

$^{19}$F NMR (376 MHz, DMSO) δ −57.51.

$^{13}$C NMR (101 MHz, DMSO) δ 174.29, 159.77, 158.81, 146.33, 141.56, 140.02, 139.65, 132.33, 129.97, 128.30, 128.19, 127.88, 126.38, 126.34, 126.27, 126.13, 123.56, 122.64, 122.60, 121.26, 119.26, 118.45, 114.96, 98.45, 67.37, 66.51, 31.86, 29.71, 22.28, 19.63, 18.69, 14.14. HRMS (ESI) calculated for $C_{30}H_{30}F_3NO_3$ [M+H]$^+$: 510.2250. found 510.2246.

Example 47

6-butyl-3-(2,4-dimethylphenyl)-2-methyl-7-(2-phenoxyethoxy)quinolin-4(1H)-one (40): Following general procedure F, as given in Example 7, the title compound was prepared in 64% yield. This reaction was performed in a microwave reactor at a temperature of 110° C.

$^1$H NMR (400 MHz, DMSO) δ 11.56 (s, 1H), 7.81 (s, 1H), 7.35-7.27 (m, 3H), 7.22 (d, J=8.3 Hz, 1H), 7.05-6.93 (m, 5H), 4.38 (d, J=5.9 Hz, 4H), 2.60 (t, J=7.3 Hz, 2H), 2.03 (s, 6H), 1.52 (dd, J=14.8, 7.6 Hz, 2H), 1.27-1.21 (m, 2H), 0.82 (t, J=7.3 Hz, 3H).

$^{13}$C NMR (101 MHz, DMSO) δ 173.96, 159.21, 158.41, 145.82, 140.19, 139.59, 135.53, 132.69, 131.32, 129.49, 129.09, 127.61, 125.75, 125.34, 120.78, 118.81, 118.12, 114.53, 97.98, 66.86, 66.07, 31.46, 29.28, 21.88, 19.18, 18.29, 13.74. HRMS (ESI) calculated for $C_{30}H_{33}NO_3$ [M+H]$^+$: 456.2533. found 456.2541.

Example 48

6-butyl-3-(2-fluoro-4-(trifluoromethyl)phenyl)-2-methyl-7-(2-phenoxyethoxy)quinolin-4(1H)-one (41): Following general procedure F, as given in Example 7, the title compound was prepared in 48% yield.

$^1$H NMR (400 MHz, DMSO) δ 12.38 (s, 1H), 7.90 (s, 1H), 7.71 (d, J=9.3 Hz, 1H), 7.66-7.46 (m, 2H), 7.31 (t, J=7.8 Hz, 2H), 7.11 (s, 1H), 7.05-6.79 (m, 3H), 4.43 (s, 4H), 2.74-2.52 (m, 2H), 2.23 (s, 3H), 1.53 (dd, J=14.6, 7.5 Hz, 2H), 1.28-1.19 (m, 2H), 0.82 (t, J=7.3 Hz, 3H).

$^{19}$F NMR (376 MHz, DMSO) δ −61.11, −110.84.

$^{13}$C NMR (101 MHz, DMSO) δ 172.39, 160.41 (d, J=247.45 Hz), 160.31, 158.83, 148.67, 140.11, 135.08, 130.16, 129.92, 129.69, 128.20 (d, J=16.16), 125.70, 123.90 (q, J=273.71 Hz) 121.38, 121.23, 117.38, 114.98, 113.41, 113.22, 98.69, 67.52, 66.47, 31.69, 29.76, 22.25, 18.92, 14.13. HRMS (ESI) calculated for $C_{29}H_{27}F_4NO_3$ [M+H]$^+$: 514.1999. found 514.2000.

Example 49

6-butyl-3-(4-chloro-2-methylphenyl)-2-methyl-7-(2-phenoxyethoxy)quinolin-4(1H)-one (42): Following general procedure F, as given in Example 7, the title compound was prepared in 52% yield.

¹H NMR (400 MHz, DMSO) δ 11.44 (s, 1H), 7.79 (s, 1H), 7.31 (t, J=7.6 Hz, 2H), 7.01 (dd, J=23.2, 14.6 Hz, 5H), 6.88 (d, J=7.8 Hz, 2H), 4.39 (d, J=6.0 Hz, 4H), 2.64-2.55 (m, 2H), 2.29 (s, 3H), 2.00 (d, J=14.3 Hz, 6H), 1.53 (dt, J=14.8, 7.5 Hz, 2H), 1.25 (dd, J=14.8, 7.3 Hz, 2H), 0.83 (t, J=7.3 Hz, 3H). ¹³C NMR (101 MHz, DMSO) δ 174.65, 159.50, 158.85, 146.04, 139.97, 137.59, 136.15, 133.93, 131.21, 130.61, 129.94, 127.77, 126.48, 126.25, 121.22, 120.41, 118.60, 114.98, 98.34, 67.28, 66.52, 31.93, 29.72, 22.31, 21.15, 19.76, 18.78, 14.18. HRMS (ESI) calculated for $C_{29}H_{30}ClNO_3$ [M+H]⁺: 476.1987. found 476.1984.

Example 50

6-butyl-3-(3,5-dimethylisoxazol-4-yl)-2-methyl-7-(2-phenoxyethoxy)quinolin-4(1H)-one (43): Following general procedure F, as given in Example 7, the title compound was prepared in 10% yield. This reaction was performed in a microwave reactor at a temperature of 110° C.

¹H NMR (400 MHz, DMSO) δ 11.70 (s, 1H), 7.79 (s, 1H), 7.30 (dd, J=8.4, 7.5 Hz, 2H), 7.01-6.92 (m, 4H), 4.39 (d, J=2.3 Hz, 4H), 2.63-2.57 (m, 2H), 2.16 (d, J=2.8 Hz, 6H), 1.98 (s, 3H), 1.55-1.50 (m, 2H), 1.24 (d, J=7.5 Hz, 2H), 0.84 (d, J=7.3 Hz, 3H). ¹³C NMR (101 MHz, DMSO) δ 174.30, 165.72, 160.26, 159.35, 158.41, 147.95, 139.57, 129.50, 127.91, 125.68, 120.79, 117.75, 114.55, 110.87, 107.78, 98.12, 66.94, 66.08, 31.41, 29.24, 21.85, 18.21, 13.73, 11.24, 10.23. HRMS (ESI) calculated for $C_{27}H_{30}N_2O_4$ [M+H]⁺: 447.2278. found 447.2289.

We claim:

1. A compound having the Formula I or II:

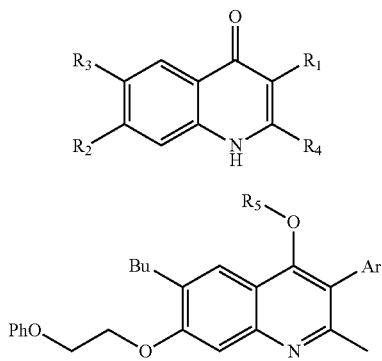

wherein, in Formula I:
- $R_1$ is H, ethyl, an aryl, carboxymethyl, or a halogen;
- $R_2$ is 2-phenoxyethoxy, methoxymethoxy, 3-hydroxy-propoxy, 2-ethyl-3-oxo-butyricacid, 2-morpholino-4-yl-ethoxy-, 2-dimethylamino-ethoxy, or 3-(4-phenyl-piperazin-1-yl)-propoxy;
- $R_3$ is H, butyrate, a halogen, methyl, or methoxy; and
- $R_4$ is H or methyl, and wherein, when $R_2$ is methoxymethoxy, $R_3$ is a halogen; and wherein in Formula II:
- $R_5$ is an H or an alkyl, and
- Ar is an aromatic group selected from the group consisting of: phenyl, pyridin-4-yl, pyridin-3-yl, 4-(trifluoromethyl)phenyl, 4-fluorophenoxyphenyl, 4-((4-(trifluoromethoxy)methyl)phenyl), (2-methyl-4-(4-(trifluoromethoxy)phenoxy)phenyl), (2-methyl-4-(trifluoromethyl)phenyl), 2,4-dimethylphenyl, (2-fluoro-4-(trifluoromethyl)phenyl), (4-chloro-2-methylphenyl), and (3,5-dimethylisooxazol-4-yl).

2. The compound of claim 1 having the Formula I.

3. A compound having the Formula I,

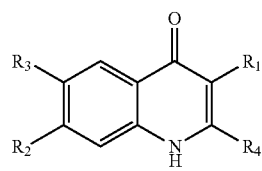

wherein:
- $R_1$ is H, ethyl, an aryl, carboxymethyl, or a halogen;
- $R_2$ is 2-phenoxyethoxy, methoxymethoxy, 3-hydroxy-propoxy, 2-ethyl-3-oxo-butyricacid, 2-morpholino-4-yl-ethoxy-, 2-dimethylamino-ethoxy, or 3-(4-phenyl-piperazin-1-yl)-propoxy;
- $R_3$ is H, butyl, a halogen, methyl, or methoxy; and
- $R_4$ is H or methyl, and wherein the compound is selected from the group consisting of:
6-butyl-2-methyl-7-(2-phenoxyethoxy)quinolin-4(1H)-one (15), 6-butyl-3-ethyl-2-methyl-7-(2-phenoxyethoxy)quinolin-4(1H)-one (16), 6-chloro-3-ethyl-2-methyl-7-(2-phenoxy-ethoxy)-1H-quinolin-4-one (17), 3-ethyl-2,6-dimethyl-7-(2-phenoxy-ethoxy)-1H-quiolin-4-one (18), 6-chloro-3-ethyl-7-methoxymethoxy-2-methyl-1H-quinoline-4-one (20), 6-chloro-3-ethyl-7-(3-hydroxy-propoxy)-2-methyl-1H-quinolin-4-one (21), 2-ethyl-3-oxo-butyricacid-3-(6-chloro-3-ethyl-2-methyl-4-oxo-1,4-dihydro-quinolin-7-yloxy)-propyl ester (22), 6-chloro-3-ethyl-2-methyl-7-(2-morpholin-4-yl-ethoxy)-1H-quinolin-4-one (23), 6-chloro-7-(2-dimethylamino-ethoxy)-3-ethyl-2-methyl-1H-quinolin-4-one (24), 6-bromo-3-ethyl-2-methyl-7-(2-phenoxy-ethoxy)-1H-quinolin-4-one (25), and 6-chloro-3-ethyl-2-methyl-7[3-(4-phenyl-piperazin-1-yl)-propoxy]-1H-quinolin-4-one (26).

4. The compound of claim 1 having the Formula II.

5. The compound of claim 1, wherein $R_5$ is methyl or ethyl.

6. The compound of claim 4, wherein the compound is selected from the group consisting of:
6-butyl-2-methyl-7-(2-phenoxyethoxy)-3-phenylquinolin-4(1H)-one (31), 6-butyl-2-methyl-7-(2-phenoxyethoxy)-3-(pyridin-4-yl)quinolin-4(1H)-one (32), 6-butyl-2-methyl-7-(2-phenoxyethoxy)-3-(pyridin-3-yl)quinolin-4(1H)-one (33), 6-butyl-2-methyl-7-(2-phenoxyethoxy)-3-(4-(trifluoromethyl)phenyl)quinolin-4(1H)-one (34), 6-butyl-2-methyl-7-(2-phenoxyethoxy)-3-(4-(trifluoromethoxy)phenyl)quinolin-4(1H)-one (35), 6-butyl-3-(3-(4-fluorophenoxy)phenyl)-2-methyl-7-(2phenoxyethoxy)quinolin-4(1H)-one (36), 6-butyl-2-methyl-7-(2-phenoxyethoxy)-3-(4-((4-(trifluoromethoxy)phenoxy)methyl)phenyl) quinolin-4(1H)-one (37), 6-butyl-2-methyl-3-(2-methyl-4-(4-(trifluoromethoxy)phenoxy)phenyl)-7-(2-phenoxyethoxy)-quinolin-4(1H)-one (38), 6-butyl-2-methyl-3-(2-methyl-4-(trifluoromethyl)phenyl)-7-(2-phenoxyethoxy)quinolin-4(1H)-one (39), 6-butyl-3-(2,4-dimethylphenyl)-2-methyl-7-(2-phenoxyethoxy)quinolin-4(1H)-one (40), 6-butyl-3-(2-fluoro-4-(trifluoromethyl)phenyl)-2-methyl-7-(2-phenoxyethoxy)quinolin-4(1H)-one (41), 6-butyl-3-(4-chloro-2-methylphenyl)-2-methyl-7-(2- phenoxyethoxy)quinolin-4(1H)-one (42), and 6-butyl-3-(3,5-dimethylisoxazol-4-yl)-2-methyl-7-(2-phenoxyethoxy)quinolin-4(1H)-one (43).

7. A pharmaceutically acceptable composition comprising a therapeutic amount of a compound selected from the group consisting of: 6-butyl-2-methyl-7-(2-phenoxyethoxy)quinolin-4(1H)-one (15), 6-butyl-3-ethyl-2-methyl-7-(2-phenoxyethoxy)quinolin-4(1H)-one (16), 6-chloro-3-ethyl-2-methyl-7-(2-phenoxy-ethoxy)-1H-quinolin-4one (17), 3-ethyl-2,6-dimethyl-7-(2-phenoxy-ethoxy)-1H-quiolin-4-one (18) 6-chloro-3-ethyl-7-methoxymethoxy-2-methyl-1H-quinoline-4-one (20), 6-chloro-3-ethyl-7-(3-hydroxy-propoxy)-2-methyl-1H-quinolin-4-one (21), 2-ethyl-3-oxo-butyricacid-3-(6-chloro-3-ethyl-2-methyl-4-oxo-1,4-dihydro-quinolin-7-yloxy)-propyl ester (22), 6-chloro-3-ethyl-2-methyl-7-(2-morpholin-4-yl-ethoxy)-1H-quinolin-4-one (23), 6-chloro-7-(2-dimethylamino-ethoxy)-3-ethyl-2-methyl-1H-quinolin-4-one (24), 6-bromo-3-ethyl-2-methyl-7-(2-phenoxy-ethoxy)-1H-quinolin-4-one (25), 6-chloro-3-ethyl-2-methyl-7-[3-(4-phenyl-piperazin-1-yl)-propoxy]-1H-quinolin-4-one (26), 6-butyl-2-methyl-7-(2-phenoxyethoxy)-3-phenylquinolin-4(1H)-one (31), 6-butyl-2-methyl-7-(2-phenoxyethoxy)-3-(pyridin-4-yl)quinolin-4 (1H)-one (32), 6-butyl-2-methyl-7-(2-phenoxyethoxy)-3-(pyridin-3-yl)quinolin-4(1H)-one (33), 6-butyl-2-methyl-7-(2-phenoxyethoxy)-3-(4-(trifluoromethyl)phenyl)quinolin-4 (1H)-one (34), 6-butyl-2-methyl-7-(2-phenoxyethoxy)-3-(4-(trifluoromethoxy)phenyl)quinolin-4(1H)-one (35), 6-butyl-3-(3-(4-fluorophenoxy)phenyl)-2-methyl-7-(2phenoxyethoxy)quinolin-4(1H)-one (36), 6-butyl-2-methyl-7-(2-phenoxyethoxy)-3-(4-((4-(trifluoromethoxy)phenoxy)methyl)phenyl) quinolin-4(1H)-one (37), 6-butyl-2-methyl-3-(2-methyl-4-(4-(trifluoromethoxy)phenoxy)phenyl)-7-(2-phenoxyethoxy)-quinolin-4(1H)-one (38), 6-butyl-2-methyl-3-(2-methyl-4-(trifluoromethyl)phenyl)-7-(2-phenoxyethoxy)quinolin-4(1H)-one (39), 6-butyl-3-(2,4-dimethylphenyl)-2-methyl-7-(2-phenoxyethoxy)quinolin-4(1H)-one (40), 6-butyl-3-(2-fluoro-4-(trifluoromethyl)phenyl)-2-methyl-7-(2-phenoxyethoxy)quinolin-4(1H)-one (41), 6-butyl-3-(4-chloro-2-methylphenyl)-2-methyl-7-(2-phenoxyethoxy)quinolin-4(1H)-one (42), and 6-butyl-3-(3,5-dimethylisoxazol-4-yl)-2-methyl-7-(2-phenoxyethoxy) quinolin-4(1H)-one (43) that when administered to a recipient animal or human subject as a single dose or as multiple doses is effective in reducing or preventing a malarial infection in the subject.

8. The pharmaceutically acceptable composition of claim 7, further comprising a pharmaceutically acceptable carrier.

9. A method of reducing the viability of a population of malarial parasites, wherein the method comprises administering to an animal or human subject a therapeutically effective amount of a pharmaceutically acceptable composition comprising a compound selected from the group consisting of: 6-butyl-2-methyl-7-(2-phenoxyethoxy)quinolin-4(1H)-one (15), 6-butyl-3-ethyl-2-methyl-7-(2-phenoxyethoxy) quinolin-4(1H)-one (16), 6-chloro-3-ethyl-2-methyl-7-(2-phenoxy-ethoxy)-1H-quinolin-4-one (17), 3-ethyl-2,6-dimethyl-7-(2-phenoxy-ethoxy)-1H-quiolin-4-one (18), 6-chloro-3-ethyl-7-methoxymethoxy-2-methyl-1H-quinoline-4-one (20), 6-chloro-3-ethyl-7-(3-hydroxy-propoxy)-2-methyl-1H-quinolin-4-one (21), 2-ethyl-3-oxo-butyricacid-3-(6-chloro-3-ethyl-2-methyl-4-oxo-1,4-dihydro-quinolin-7-yloxy)-propyl ester (22), 6-chloro-3-ethyl-2-methyl-7-(2-morpholin-4-yl-ethoxy)-1H-quinolin-4-one (23), 6-chloro-7-(2-dimethylamino-ethoxy)-3-ethyl-2-methyl-1H-quinolin-4-one (24), 6-bromo-3-ethyl-2-methyl-7-(2-phenoxy-ethoxy)-1H-quinolin-4-one (25), 6-chloro-3-ethyl-2-methyl-7-[3-(4-phenyl-piperazin-1-yl)-propoxy]-1H-quinolin-4-one (26), 6-butyl-2-methyl-7-(2-phenoxyethoxy)-3-phenylquinolin-4(1H)-one (31), 6-butyl-2-methyl-7-(2-phenoxyethoxy)-3-(pyridin-4-yl)quinolin-4 (1H)-one (32), 6-butyl-2-methyl-7-(2-phenoxyethoxy)-3-(pyridin-3-yl)quinolin-4(1H)-one (33), 6-butyl-2-methyl-7-(2-phenoxyethoxy)-3-(4-(trifluoromethyl)phenyl)quinolin-4 (1H)-one (34), 6-butyl-2-methyl-7-(2-phenoxyethoxy)-3-(4-(trifluoromethoxy)phenyl)quinolin-4(1H)-one (35), 6-butyl-3-(3-(4-fluorophenoxy)phenyl)-2-methyl-7-(2phenoxyethoxy)quinolin-4(1H)-one (36), 6-butyl-2-methyl-7-(2-phenoxyethoxy)-3-(4-((4-(trifluoromethoxy)phenoxy)methyl)phenyl) quinolin-4(1H)-one (37), 6-butyl-2-methyl-3-(2-methyl-4-(4-(trifluoromethoxy)phenoxy)phenyl)-7-(2-phenoxyethoxy)-quinolin-4(1H)-one (38), 6-butyl-2-methyl-3-(2-methyl-4-(trifluoromethyl)phenyl)-7-(2-phenoxyethoxy)quinolin-4(1H)-one (39), 6-butyl-3-(2,4-dimethylphenyl)-2-methyl-7-(2-phenoxyethoxy)quinolin-4(1H)-one (40), 6-butyl-3-(2-fluoro-4-(trifluoromethyl)phenyl)-2-methyl-7-(2-phenoxyethoxy)quinolin-4(1H)-one (41), 6-butyl-3-(4-chloro-2-methylphenyl)-2-methyl-7-(2-phenoxyethoxy)quinolin-4(1H)-one (42), and 6-butyl-3-(3,5dimethylisoxazol-4-yl)-2-methyl-7-(2-phenoxyethoxy) quinolin-4(1H)-one (43).

10. The method of claim 9, wherein the compound is selected from the group consisting of:
6-butyl-2-methyl-7-(2-phenoxyethoxy)quinolin-4(1H)-one (15), 6-butyl-3-ethyl-2-methyl-7-(2-phenoxyethoxy)quinolin-4(1H)-one (16), 6-chloro-3-ethyl-2-methyl-7-(2-phenoxy-ethoxy)-1H-quinolin-4-one (17), 3-ethyl-2,6-dimethyl-7-(2-phenoxy-ethoxy)-1H-quiolin-4-one (18), (19), 6-chloro-3-ethyl-7-methoxymethoxy-2-methyl-1H-quinoline-4-one (20), 6-chloro-3-ethyl-7-(3-hydroxy-propoxy)-2-methyl-1H-quinolin-4-one (21), 2-ethyl-3-oxo-butyricacid-3-(6-chloro-3-ethyl-2-methyl-4-oxo-1,4-dihydro-quinolin-7-yloxy)-propyl ester (22), 6-chloro-3-ethyl-2-methyl-7-(2-morpholin-4-yl-ethoxy)-1H-quinolin-4-one (23), 6-chloro-7-(2-dimethylamino-ethoxy)-3-ethyl-2-methyl-1H-quinolin-4-one (24), 6-bromo-3-ethyl-2-methyl-7-(2-phenoxy-ethoxy)-1H-quinolin-4-one (25), and 6-chloro-3-ethyl-2-methyl-7-[3-(4-phenyl-piperazin-1-yl)-propoxy]-1H-quinolin-4-one (26).

11. The method of claim 9, wherein the compound is selected from the group consisting of: 6-butyl-2-methyl-7-(2-phenoxyethoxy)-3-phenylquinolin-4(1H)-one (31), 6-butyl-2-methyl-7-(2-phenoxyethoxy)-3-(pyridin-4-yl)quinolin-4 (1H)-one (32), 6-butyl-2-methyl-7-(2-phenoxyethoxy)-3-(pyridin-3-yl)quinolin-4(1H)-one (33), 6-butyl-2-methyl-7-(2-phenoxyethoxy)-3-(4-(trifluoromethyl)phenyl)quinolin-4 (1H)-one (34), 6-butyl-2-methyl-7-(2-phenoxyethoxy)-3-(4-(trifluoromethoxy)phenyl)quinolin-4(1H)-one (35), 6-butyl-3-(3-(4-fluorophenoxy)phenyl)-2-methyl-7-(2phenoxyethoxy)quinolin-4(1H)-one (36), 6-butyl-2-methyl-7-(2-phenoxyethoxy)-3-(4-((4-(trifluoromethoxy)phenoxy)methyl)phenyl) quinolin-4(1H)-one (37), 6-butyl-2-methyl-3-(2-methyl-4-(4-(trifluoromethoxy)phenoxy)phenyl)-7-(2-phenoxyethoxy)-quinolin-4(1H)-one (38), 6-butyl-2-methyl-3-(2-methyl-4-(trifluoromethyl)phenyl)-7-(2-phenoxyethoxy)quinolin-4(1H)-one (39), 6-butyl-3-(2,4-dimethylphenyl)-2-methyl-7-(2-phenoxyethoxy)quinolin-4(1H)-one (40), 6-butyl-3-(2-fluoro-4-(trifluoromethyl)phenyl)-2-methyl-7-(2-phenoxyethoxy)quinolin-4(1H)-one (41), 6-butyl-3-(4-chloro-2-methylphenyl)-2-methyl-7-(2- phenoxyethoxy)quinolin-4(1H)-one (42), and 6-butyl-3-(3,5-dimethylisoxazol-4-yl)-2-methyl-7-(2-phenoxyethoxy)quinolin-4(1H)-one (43).

* * * * *